United States Patent [19]

Sarges

[11] Patent Number: 4,547,501

[45] Date of Patent: Oct. 15, 1985

[54] METHOD OF USING [1,2,4]TRIAZOLO[4,3-A]QUINOXALINE-4-AMINE DERIVATIVES AS ANTIDEPRESSANT AND ANTIFATIGUE AGENTS

[75] Inventor: Reinhard Sarges, Mystic, Conn.

[73] Assignee: Pfizer Inc., New York, N.Y.

[21] Appl. No.: 659,394

[22] Filed: Oct. 10, 1984

Related U.S. Application Data

[63] Continuation-in-part of Ser. No. 528,361, Sep. 2, 1983, Pat. No. 4,495,187, which is a continuation-in-part of Ser. No. 434,789, Oct. 18, 1982, abandoned.

[51] Int. Cl.$^4$ .................. A61K 31/50; A61K 31/495
[52] U.S. Cl. .................................................. 514/250
[58] Field of Search ........................ 424/250; 514/250

[56] References Cited

U.S. PATENT DOCUMENTS

3,839,569  10/1974  Dreikorn et al. .................. 424/258
4,008,322   2/1977  Dreikorn et al. .................. 424/250

FOREIGN PATENT DOCUMENTS

2249350  4/1974  Fed. Rep. of Germany .

*Primary Examiner*—Stanley J. Friedman
*Attorney, Agent, or Firm*—Charles J. Knuth; Peter C. Richardson

[57] ABSTRACT

A series of novel [1,2,4]triazolo[4,3-a]quinoxaline-4-amine derivatives wherein the amine group is optionally substituted with lower alkyl, phenylalkyl having up to three carbon atoms in the alkyl moiety or alkanoyl having from two to five carbon atoms, or the amine group alternatively completes a piperazino ring, the quinoxaline ring is optionally substituted with fluorine, chlorine, bromine or methoxy, and the triazolo ring is optionally substituted with lower alkyl, lower perfluoroalkyl or phenyl are disclosed. These novel compounds are useful for treatment of symptoms associated with depression. Also disclosed are pharmaceutical compositions containing the novel compounds of this invention and a method of using the compounds in the treatment of depression and fatigue.

25 Claims, No Drawings

METHOD OF USING [1,2,4]TRIAZOLO[4,3-A]QUINOXALINE-4-AMINE DERIVATIVES AS ANTIDEPRESSANT AND ANTIFATIGUE AGENTS

CROSS REFERENCE TO RELATED APPLICATION

This application is a continuation-in-part of co-pending application Ser. No. 528,361, filed Sept. 2, 1983, now U.S. Pat. No. 4,495,187, which, in turn, is a continuation-in-part of co-pending application Ser. No. 434,789, filed Oct. 18, 1982 and now abandoned.

BACKGROUND OF THE INVENTION

This invention relates to a series of novel [1,2,4]triazolo[4,3-a]quinoxaline-4-amine derivatives and their pharmaceutically acceptable acid addition salts which are useful as antidepressant and anti-fatigue agents.

An intensive search has been undertaken for agents which are effective in reducing the symptoms of depression and fatigue in mammals.

U.S. Pat. No. 3,839,569 and West German Pat. No. 2,249,350, respectively, disclose the use of s-triazolo[4,3-a]quinolines and 1H-imidazo[4,5-b]-quinoxalines as agricultural fungicides. U.S. Pat. No. 4,008,322 discloses the use of a series of triazolo[4,3-a]quinoxaline derivatives for control of rice blast caused by the phytopathogen *Piricularia oryzae*.

SUMMARY OF THE INVENTION

The present invention relates to novel [1,2,4]triazolo[4,3-a]quinoxaline-4-amine derivatives useful as antidepressant and anti-fatigue agents. Specifically, the compounds of the present invention are of the formula:

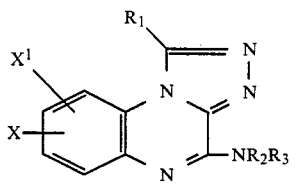
(I)

and the pharmaceutically acceptable acid addition salts thereof, wherein

X and $X^1$ are each selected from the group consisting of hydrogen, fluorine, chlorine, bromine and methoxy;
$R_1$ is selected from the group consisting of hydrogen, lower alkyl, lower perfluoroalkyl and phenyl; and
$R_2$ and $R_3$ are each selected from the group consisting of hydrogen, lower alkyl, phenylalkyl having up to three carbon atoms in the alkyl moiety and alkanoyl having from two to five carbon atoms, provided that at least one of $R_2$ and $R_3$ is always other than hydrogen when X and $X^1$ are each hydrogen and $R_1$ is hydrogen or methyl; or $R_2$ and $R_3$, when taken together, complete a piperazino ring.

For purposes of the present specification and claims, by lower alkyl is meant alkyl having 1 to 4 carbon atoms and by lower perfluoroalkyl is meant perfluoroalkyl having from 1 to 4 carbon atoms like trifluoromethyl and pentafluoroethyl, etc.

One group of compounds of interest are those wherein X and $X^1$ are each hydrogen, $R_1$ is hydrogen, and $R_2$ and $R_3$ are each lower alkyl. Preferred compounds include those wherein $R_2$ and $R_3$ are both ethyl.

Another group of compounds of the present invention are those wherein X and $X^1$ are each hydrogen, $R_1$ is ethyl and $R_3$ is lower alkyl. Preferred compounds are those wherein $R_2$ is hydrogen and $R_3$ is ethyl.

Still another group of compounds of the present invention are those wherein X and $X^1$ are each hydrogen, $R_1$ is lower alkyl and $R_3$ is acetyl. Preferred compounds include those wherein $R_1$ is ethyl and $R_2$ is hydrogen, ethyl or acetyl.

A further group of compounds of interest of the present invention are those wherein at least one of X and $X^1$ is fluorine, $R_1$ is hydrogen or trifluoromethyl, $R_2$ is hydrogen and $R_3$ is hydrogen, lower alkyl or alkanoyl having from two to five carbon atoms; or, alternatively, wherein at least one of X and $X^1$ is chlorine, $R_1$ is lower alkyl or trifluromethyl, $R_2$ is hydrogen and $R_3$ is hydrogen, lower alkyl or alkanoyl having from two to five carbon atoms.

Also embraced by the present invention are pharmaceutical compositions comprising an antidepressant, antifatigue effective amount of a compound of Formula I or a pharmaceutically acceptable acid addition salt thereof, together with a pharmaceutically acceptable carrier or diluent. Preferred pharmaceutical compositions are those containing the preferred compound of Formula I as described hereinabove.

The present invention also comprises a method of treating depression and fatigue in a mammal in need of such treatment, which comprises administering to said mammal an antidepressant/antifatigue effective amount of a compound of formula I or a pharmaceutically acceptable acid addition salt thereof. Preferred compounds for use in this method of treatment are the preferred compounds of formula I as described hereinabove.

DETAILED DESCRIPTION OF THE INVENTION

The majority of the novel compounds of formula I may be prepared by the reaction sequence shown in reaction scheme I. The numbering of the phenyl and the two heterocyclic rings in scheme I is that employed throughout the specification.

In scheme I, a compound of formula IV, a quinoxaline derivative wherein X and $X^1$ are each hydrogen, fluorine, chlorine, bromine or methoxy, with the proviso that X is always hydrogen when said quinoxaline derivative is monosubstitued in the benzene ring, is treated with an excess molar amount of hydrazine hydrate in a polar, reaction-inert organic solvent such as an alkanol having from 1 to 3 carbons, preferably ethanol, at room temperature for a period of about 18–24 hours to form an intermediate compound of formula III.

The intermediate compound of formula III may then be subsequently converted to the corresponding intermediate of formula IIA, wherein $R_1$ is other than lower perfluoroalkyl, by treatment with an appropriate alkyl orthoalkanoate or alkyl orthobenzoate, as the case may be, at a temperature between about 80° and 120° C. for about 1 to 24 hours. In the resulting compound of formula IIA, $R_1$ (as hydrogen or alkyl) is determined by the particular orthoalkanoate employed in the synthesis. Thus, for example, when triethyl orthoformate is used, $R_1$ is hydrogen, when triethyl orthopropionate is used, $R_1$ is ethyl and when triethyl orthoisobutyrate is used, $R_1$ is isopropyl.

The intermediate compound of formula III may also be converted to the corresponding intermediate of formula IIA wherein $R_1$ is lower perfluoroalkyl by treatment with an excess molar amount of an appropriate perfluoroalkanoic acid, such as trifluoroacetic acid or pentafluoropropionic acid, etc., as the case may be, in a conventional manner to yield the corresponding 4-hydroxy-1-perfluoroalkyl-[1,2,4]triazolo[4,3-a]quinoxaline, followed by treatment of the latter type compound with phosphorus oxychloride in the presence of a tertiary amine, such as triethylamine, at elevated temperatures to yield the corresponding 4-chloro compound.

Intermediate IIA (wherein $R_1$ is hydrogen, lower alkyl, lower perfluoroalkyl or phenyl) is then converted to a [1,2,4]triazolo[4,3-a]quinoxaline-4-amine derivative of formula IA, wherein $R_2$ and $R_3$ are each as previously defined except that they are other than alkanoyl, by treatment with an excess molar amount of an amine of the formula $HNR_2R_3$ in a reaction-inert organic solvent, preferably N,N-dimethylformamide, at a temperature between about 0° and 60° C. for about 2 to 24 hours. For example, the preferred compounds of formula IA in which $R_2$ and $R_3$ are both ethyl are prepared by treating the appropriate compound of formula IIA with diethylamine in N,N-dimethylformamide at room temperature for 2-3 hours. Likewise, preferred compounds of formula IA wherein $R_2$ is hydrogen and $R_3$ is ethyl are prepared by treating a compound of formula IIA with monoethylamine in N,N-dimethylformamide at room temperature for 4 to 5 hours.

[1,2,4]Triazolo[4,3-a]quinoxaline-4-amine derivatives of the formula IA wherein at least one of $R_2$ and $R_3$ is alkanoyl having from two to five carbon atoms are prepared from the corresponding compounds of formula IA where at least one of $R_2$ and $R_3$ is hydrogen by contacting the latter with the appropriate alkanoic acid anhydride under substantially anhydrous conditions. This reaction can be carried out in the presence of an organic base, such as a tertiary amine, as catalyst (although this is not absolutely necessary) at a temperature ranging from about 20° C. up to about 140° C. for a period of about one-half to about 24 hours. The molar ratio of acid anhydride to the 4-amino starting material should be at least about 1:1 and preferably from about 4:1 to about 25:1, while the amount of tertiary amine employed is normally about 25 to 150% by weight of the aforesaid acylating agent (the tertiary amine may be used as the reaction solvent by merely employing an excess of same). Although it is quite possible and even, in some instances, highly desirable to carry out the reaction in the absence of a solvent, there may be times when the use of a suitable reaction-inert organic solvent is clearly indicated. Suitable organic solvents for use in this connection include neutral, reaction-inert anhydrous organic solventts, such as acetone, methyl ethyl ketone, benzene, toluene, xylene, dioxane, tetrahydrofuran, methylene chloride, chloroform, ethylene dichloride, tetrachloroethane, methyl acetate, ethyl acetate, isopropyl acetate, methyl propionate, ethyl propionate, diethyl ether, diisopropyl ether, di-n-propyl ether and the like. However, as previously indicated, the reaction is ordinarily conducted in the absence of such a solvent by merely employing an excess of acid anhydride. Similarly, an excess of the tertiary amine reagent may also serve as a solvent. Preferred tertiary amines for use as solvents and/or as catalytic reagents in this reaction include triethylamine, dimethylaniline, pyridine, picoline, lutidine, collidine and quinoline.

The starting materials of formula IV wherein X and $X^1$ are each hydrogen are well known in the art. Compounds of formula IV wherein $X^1$ is methoxy may be prepared by the method of G. W. H. Cheeseman [*J. Chem. Soc.*, p. 1170 (1962)] wherein 4-methoxy-o-phenylenediamine hydrochloride is treated with at least an equimolar amount of diethyl oxalate and diethylamine under an atmosphere of inert gas, preferably nitrogen, at reflux temperature for about 2 to 3 hours, followed by treatment with phosphorus oxychloride in a tertiary amine, preferably dimethylaniline, at reflux temperatures for 1-2 hours.

In reaction scheme II, a quinoxaline derivative of the formula IV, wherein X is fluorine, chlorine, bromine or methoxy and $X^1$ is hydrogen, is treated with sodium methoxide in an alcoholic solvent medium at slightly elevated temperatures (e.g., 40°-60° C.) for a period of approximately 6-18 hours to form the corresponding 2-chloro-3-methoxyquinoxaline derivative of formula V, which is then treated with hydrazine hydrate in the same manner as before to yield the corresponding 2-hydrazino-3-methoxyquinoxaline derivative of formula VI. The latter intermediate (VI) is then subsequently converted to the desired 7-substituted 4-methoxy-[1,2,4]triazolo[4,3-a]quinoxaline derivative of formula VII by use of an appropriate ortho ester, or with perfluoroalkanoic acid, in the same manner as previously described, and the latter compound is then successively converted to the corresponding 4-hydroxy (see formula VIII) and 4-chloro compounds by conventional procedure to yield a compound of structural formula IIB wherein X is as hereinbefore defined above (i.e., other than hydrogen) and $X^1$ is hydrogen. This intermediate of formula IIB then leads to the corresponding novel final products of formula IB, wherein $R^1$, $R^2$ and $R^3$ are all as previously defined and X and $X^1$ are as above, by merely employing the reaction procedures previously described in connection with the discussion of the last stages of over-all scheme I.

The pharmaceutically acceptable acid addition salts of the novel compounds of formula I are also embraced by the present invention. These salts may be readily prepared by contacting the free base with an appropriate mineral or organic acid in either aqueous solution or in a suitable organic solvent. The solid salt may then be obtained by precipitation or by evaporation of the solvent. The pharmaceutically acceptable acid addition salts of this invention include, but are not limited to, the hydrochloride, sulfate, bisulfate, mesylate, tosylate, nitrate, phosphate, acetate, lactate, maleate, fumarate, citrate, tartrate, succinate, gluconate and the like. Mesylate salts are preferred. If desired, the compounds of formula I as the free base may be formed from the acid addition salts thereof by treatment with an appropriate base, followed by extraction of the free base with a suitable organic solvent.

The compounds of formula I and the pharmaceutically acceptable acid addition salts thereof have activity as anti-depressant and anti-fatigue agents and accordingly, are of therapeutic value in the treatment of symptoms associated with depression and fatigue. The compounds may be administered to a subject in need of treatment by a variety of conventional routes of administration, including orally and parenterally. Preferably, the compounds are administered orally. In general, these compounds will be administered orally at one or more doses between about 0.1 to 100 mg./kg. of body weight of the subject to be treated per day, preferably from about 0.5 to 10 mg./kg. per day. If parenteral administration is desired, then these compounds can be given at doses between about 0.1 to 10 mg./kg. of body weight of the subject to be treated per day. Thus, for a typical adult patient, these compounds are most desirably administered in doses ranging from about 5.0 mg. up to about 800 mg. per day (usually in divided doses of up to 3-4 times/day), although some variation in dosage will necessarily occur depending upon the condition of the subject being treated and the particular compound employed, as well as on the particular route of administration chosen. In some instances, dosage levels below the lower limit of the aforesaid range may be more than adequate, while in other cases still larger dosages may be employed without causing any harmful or deleterious side effects to occur provided that such higher dose levels are first divided into several smaller doses that are to be administered throughout the day.

When the compounds of the invention are administered in the form of pharmaceutical compositions, these pharmaceutical compositions are preferably in unit dosage form as hereinafter defined. By the term "unit dosage form" is meant a physically discrete unit containing an individual quantity of the active component in association with a pharmaceutically acceptable carrier or diluent, the quantity of the active component being such that at least one unit or severable fraction of a unit is required for a single therapeutic administration. In the case of severable units, such as scored tablets, at least one severable fraction such as one-half or one-quarter of the unit may be all that is required for a single therapeutic administration. It will be appreciated that the term "unit dosage form" does not include mere solutions except when the solutions are packaged in ingestible containers, e.g., soft capsules, or have been prepared so as to be suitable for parenteral administration, e.g., in vials of solution suitable for parenteral injection.

REACTION SCHEME I

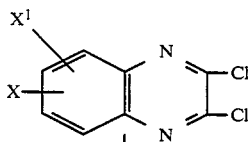

IV

↓

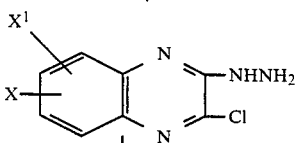

III

↓

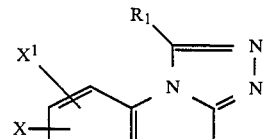

IIA
(Excludes
X$^1$ = H;
X ≠ H)

↓

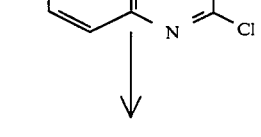

-continued

REACTION SCHEME I

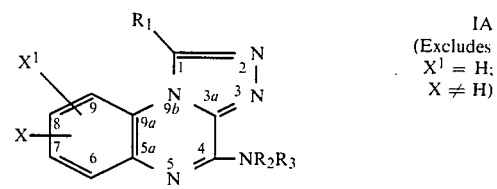

IA
(Excludes
X$^1$ = H;
X ≠ H)

REACTION SCHEME II

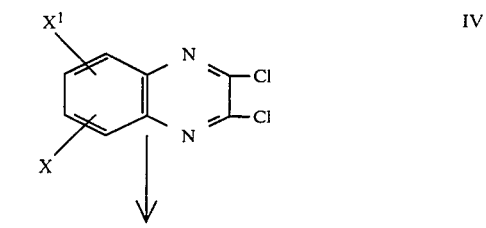

IV

↓

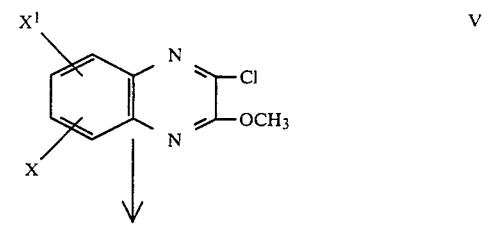

V

↓

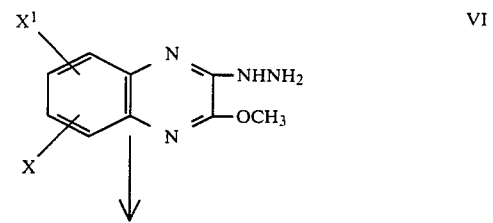

VI

↓

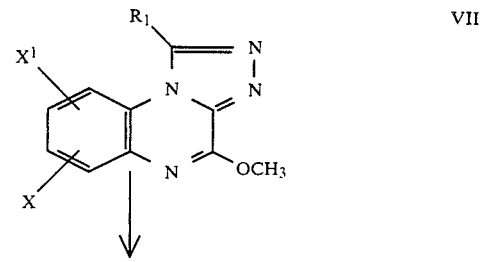

VII

↓

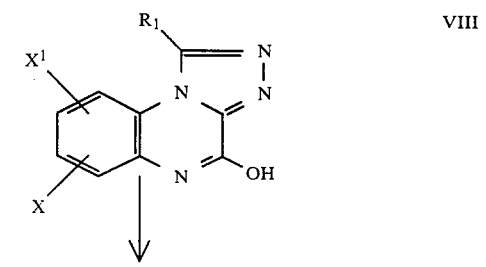

VIII

↓

-continued
REACTION SCHEME II

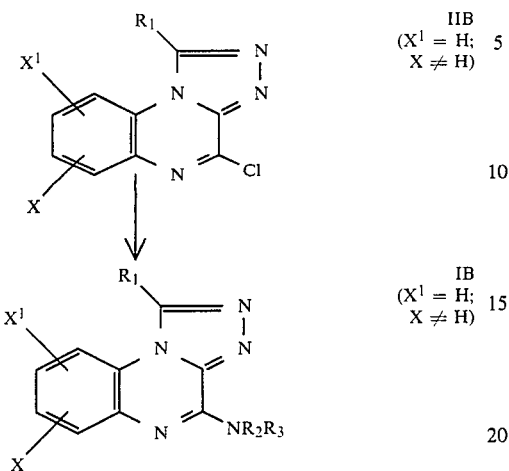

As previously indicated, the compounds of the invention may be administered alone or in combination with pharmaceutically acceptable carriers or diluents, in either single or multiple doses. Suitable pharmaceutical carriers include inert diluents or fillers, sterile aqueous solutions and various organic solvents. The pharmaceutical compositions formed by combining the novel compounds of Formula I or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, may be employed, together with various disintegrants such as starch, alginic acid and certain complex silicates, together with binding agents such as polyvinylpyrrolidone, sucrose, gelatin and acacia.

In connection with the use of the [1,2,4]triazolo-[4,3-a]quinoxaline-4-amine derivatives of this invention for the treatment of depression and fatigue, it is to be noted that they may be administered in suitable unit dosage forms which will preferably contain at least about 2.5 mg. of the active compound per dosage unit, although concentration levels in the range of from about 2.5 mg. to about 200 mg. per unit dosage per day may be employed to advantage. In this way, the active compound may be administered in divided doses up to three to four times per day to afford the desired dosage in the range previously indicated (viz., approximately 5-800 mg./day).

The activity of the compounds of the present invention as antidepressant and anti-fatigue agents is determined by various standard pharmacological tests, including, for example, Porsolt's screening model of "learned helplessness", i.e., immobility induced by forced swimming in rats [R. D. Porsolt et al., European J. Pharmacol., 47, 379 (1978)]. Pharmaceutical agents of this type which are therapeutically effective in humans are known to reduce immobility induced by forced swimming in this model.

The present invention is illustrated by the following examples. However, it should be understood that the invention is not limited to the specific details of these examples. All temperatures are in degrees centigrade.

PREPARATION A

4-Chloro-7-fluoro-[1,2,4]triazolo[4,3-a]quinoxaline (a) Preparation of
2-chloro-6-fluoro-3-methoxyquinoxaline In a flame-dried reaction flask containing a slurry of 52 g. (0.24 mole) of 2,3-dichloro-6-fluoroquinoxaline in 500 ml. of methanol under a dry nitrogen atmosphere, there was added slowly in a dropwise manner at 50° C. a solution consisting of 6.6 g. (0.29 mole) of sodium dissolved in 650 ml. of methanol. The resulting reaction mixture was then heated at 50° C. overnight (i.e., for a period of approximately 16 hours) and the clear solution so obtained was allowed to cool to room temperature (~20° C.). The reaction mixture was then concentrated in vacuo, and the residual material subsequently dissolved in chloroform, washed with water and dried over anhydrous magnesium sulfate. After removal of the drying agent by means of filtration and the solvent by means of evaporation under reduced pressure, there was ultimately obtained a liquid residue that was subsequently chromatographed on a 1000 ml. silica gel column, followed by elution with toluene. The combined fractions containing only product then gave 48.3 g. (95%) of pure 2-chloro-6-fluoro-3-methoxyquinoxaline, m.p. 93°–95° C. Mass Spectrum: m/e, 212 (P); m/e, 214 (P+2).

(b) Preparation of
6-fluoro-2-hydrazino-3-methoxyquinoxaline

To a solution consisting of 47 g. (0.22 mole) of 2-chloro-6-fluoro-3-methoxyquinoxaline dissolved in 1000 ml. of ethanol, there were added 27.6 g. (0.55 mole) of hydrazine hydrate (26.8 ml.). The resulting mixture was stirred at room temperature overnight (i.e., at ca. 20° C. for approximately 16 hours). An additional amount of hydrazine hydrate (9.0 ml.) was then added and the final reaction mixture was allowed to stir at room temperature for a period of four hours. At this point, the precipitate was filtered and washed with ethanol to ultimately afford 43.3 g. (94%) of pure 6-fluoro-2-hydrazino-3-methoxyquinoxaline, m.p. 170°–174° C. (decomp.).

(c) Preparation of
7-fluoro-4-methoxy-[1,2,4]triazolo[4,3-a]quinoxaline

A mixture consisting of 15 g. (0.072 mole) of 6-fluoro-2-hydrazino-3-methoxyquinoxaline and 250 ml. of triethyl orthoformate was heated with mechanical stirring in a preheated oil both at 100° C. overnight (~16 hours). The resulting mixture was then cooled to room temperature, and the precipitate which formed was subsequently recovered by means of suction filtration and washed with ethanol to ultimately afford 11.3 g (72%) of pure 7-fluoro-4-methoxy-[1,2,4]triazolo[4,3-a]quinoxaline, m.p. 245°–246° C. (decomp.).

(d) Preparation of
7-fluoro-4-hydroxy-[1,2,4]triazolo[4,3-a]quinoxaline

A mixture consisting of 11.3 g (0.52 mole) of 7-fluoro-4-methoxy-[1,2,4]triazolo[4,3-a]quinoxaline, 115 ml. of 1N hydrochloric acid and 345 ml. of glacial acetic acid was refluxed for a period of three hours. Upon completion of this step, the reaction mixture was cooled to room temperature and poured over ice/water. The resulting mixture was then stirred for a period of 30 minutes and thereafter filtered to remove the precipitate, which was subsequently washed with water and air-dried to ultimately afford 8.9 g. (84%) of pure 7-fluoro-4-hydroxy-[1,2,4]triazolo[4,3-a]quinoxaline, m.p.>300° C. Mass Spectrum: m/e, 204 (P).

(e) Preparation of 4-chloro-7-fluoro-[1,2,4]triazolo[4,3-a]quinoxaline

In a flame-dried reaction flask under a dry nitrogen atmosphere, there were placed 8.9 g. (0.044 mole) of 7-fluoro-4-hydroxy-[1,2,4]triazolo[4,3-a]quinoxaline and 160 ml. of phosphorus oxychloride together with 8.9 ml. of tri-n-propylamine. The reaction mixture was then refluxed overnight for approximately 16 hours and finally cooled to room temperature before being poured over ice/water with mechanical stirring. The resulting aqueous mixture was then stirred at room temperature for 30 minutes and filtered, and the solid product so obtained was subsequently washed with cold water and triturated with ethyl acetate to ultimately afford 7.0 g.(71%) of pure 4-chloro-7-fluoro-[1,2,4]triazolo[4,3-a]quinoxaline, m.p. 305°-308° C. Mass Spectrum: m/e, 222 (P); m/e, 224 (P+2).

PREPARATION B

4-Chloro-1-ethyl-7-fluoro-[1,2,4]triazolo[4,3-a]quinoxaline (a) Preparation of 1-ethyl-7-fluoro-4-methoxy-[1,2,4]triazolo-[4,3-a]quinoxaline A mixture consisting of 15 g. (0.07 mole) of 6-fluoro-2-hydrazino-3-methoxyquinoxaline, the product of Preparation A(b), and 250 ml. of triethyl orthopropionate was heated with mechanical stirring in a preheated oil bath at 100° C. overnight (~16 hours). The resulting mixture was cooled to room temperature (~20° C.) filtered and the recovered precipitate washed with ethanol to afford 11.3 g. (64%) of pure 1-ethyl-7-fluoro-4-methoxy-[1,2,4]triazolo[4,3-a]quinoxaline, m.p. 200°202° C. (decomp.).

(b) Preparation of 1-ethyl-7-fluoro-4-hydroxy-[1,2,4]triazolo-[4,3-a]quinoxaline A mixture consisting of 11.3 g (0.046 mole) of 1-ethyl-7-fluoro-4-methoxy-[1,2,4]triazolo[4,3-a]quinoxaline, 115 ml. of 1N hydrochloric acid and 345 ml. of glacial acetic acid was refluxed for a period of three hours. Upon completion of this step, the reaction mixture was cooled to room temperature and poured over ice/water. The resulting mixture was then stirred for a period of 30 minutes, filtered and the recovered solid product subsequently washed with water and air-dried to ultimately afford 6.6 g. (62%) of pure 1-ethyl-7-fluoro-4-hydroxy-[1,2,4]triazolo[4,3-a]quinoxaline, m.p.>300° C. Mass Spectrum: m/e, 232 (P); m/e, 231 (P−1).

(c) Preparation of 4-chloro-1-ethyl-7-fluoro-[1,2,4]triazolo[4,3-a]quinoxaline

In a flame-dried reaction flask under a dry nitrogen atmosphere, there were placed 6.6 g. (0.028 mole) of 1-ethyl-7-fluoro-4-hydroxy-[1,2,4]triazolo[4,3-a]quinoxaline and 120 ml. of phosphorus oxychloride together with 6.6 ml. of tri-n-propylamine. The reaction mixture was then refluxed overnight for approximately 16 hours and finally cooled to room temperature before being poured over ice/water with mechanical stirring. The resulting aqueous mixture was then stirred at room temperature for 30 minutes and filtered, and the solid product so obtained was subsequently washed with cold water and then dissolved in ethyl acetate. The latter organic solution was then successively washed with water, saturated aqueous sodium bicarbonate solution and saturated brine before being dried over anhydrous magnesium sulfate. After removal of the drying agent by means of filtration and the solvent by means of evaporation under reduced pressure, there was ultimately obtained a tan solid product which was subsequently triturated with diethyl ether to yield 4 g. (57%) of pure 4-chloro-1-ethyl-7-fluoro-[1,2,4]triazolo[4,3-a]quinoxaline, m.p. 203°-205° C. Mass Spectrum: m/e, 250 (P); m/e, 252 (P+2); m/e, 249 (P−1).

PREPARATION C 4,7-Dichloro-[1,2,4]triazolo[4,3-a]quinoxaline (a) Preparation of 2,3-dihydroxy-6-chloroquinoxaline A mixture consisting of 100 g. (0.07 mole) of 4-chloro-1,2-phenylenediamine and 750 ml. of diethyl oxalate was refluxed overnight and for a period of approximately 16 hours. Upon completion of this step, the reaction mixture was cooled to room temperature (~20° C.), filtered and the recovered product subsequently washed with ethanol and air-dried to constant weight to ultimately afford 140 g. of pure 2,3-dihydroxy-6-chloroquinoxaline, m.p.>260° C.

(b) Preparation of 2,3,6-trichloroquinoxaline

A mixture consisting of 140 g. (0.70 mole) of 2,3-dihydroxy-6-chloroquinoxaline and 326 ml. (3.50 mole) of phosphorus oxychloride was refluxed overnight (~16 hours) and then poured over ice. The resulting aqueous mixture was then filtered, and the recovered product subsequently washed with water and air-dried prior to being dissolved in chloroform. The latter organic solution was then washed with saturated brine and air-dried over anhydrous magnesium sulfate. After removal of the drying agent by means of filtration and the solvent by means of evaporation under reduced pressure, there was ultimately obtained a thick slurry which was recrystallized from chloroform/ethanol to afford 120g. (74%) of pure 2,3,6-trichloroquinoxaline, m.p. 139°-142° C. Mass Spectrum: m/e, 232 (P); m/e, 234 (P+2); m/e, 236 (P+4).

(c) Preparation of 2,6-dichloro-3-methoxyquinoxaline

A slurry consisting of 11.7 g. (0.05 mole) of 2,3,6-trichloroquinoxaline in 140 ml. of methanol was heated to 50° C., at which point there was added thereto in a dropwise manner a solution consisting of 1.4 g. (0.06 mole) of sodium dissolved in 140 ml. of methanol over a period of six hours. The resulting mixture was then heated at 50° C. overnight (~16 hours), followed by a further addition of 140 mg. of sodium in 20 ml. of methanol over a period of one hour. The final reaction mixture was then heated at 50° C. for a period of two hours and cooled to room temperature. Upon completion of this step, the spent mixture was concentrated in vacuo and dissolved in chloroform/water. The organic phase was separated and saved, and the aqueous phase further extracted with chloroform. The various organic (i.e., chloroform) extracts were combined and successively washed with fresh portions of water and saturated brine, followed by drying over anhydrous magnesium sulfate. After removal of the drying agent by means of filtration and the solvent by means of evaporation under reduced pressure, the residue was chromatographed on a column of 250 ml. of silica gel and eluted with toluene. Like fractions were combined to ultimately afford a white solid consisting of 9.8 g. (86%) of pure 2,6-dichloro-3-methoxyquinoxaline, m.p. 92°–95° C.

(d) Preparation of 6-chloro-2-hydrazino-3-methoxyquinoxaline

A mixture of 4.9 g. (0.02 mole) of 2,6-dichloro-3-methoxyquinoxaline and 2.7 g. (0.053 mole) of hydrazine hydrate (2.6 ml.) in 75 ml. of ethanol was stirred at room temperature overnight (i.e., at ca. 20° C. for approximately 16 hours). Upon completion of this step, the resulting mixture was filtered and the recovered precipitate was washed with ethanol to ultimately afford 4.4 g. (98%) of pure 6-chloro-2-hydrazino-3-methoyquinoxaline, m.p. 175°–179° C. (decomp.). Mass Spectrum: m/e, 224 (P); m/e, 226 (P+2).

(e) Preparation of 7-chloro-4-methoxy-[1,2,4]triazolo[4,3-a]quinoxaline

A mixture consisting of 1.4 g. (0.0062 mole) of 6-chloro-2-hydrazino-3-methoxyquinoxaline and 20 ml. of triethyl orthoformate was heated with mechanical stirring in a preheated oil bath at 100° C. overnight ($\sim$16 hours). The resulting mixture was then cooled to room temperature, and the precipitate which formed was subsequently recovered by means of suction filtration and washed with ethanol to ultimately afford 1.0 g. (69%) of pure 7-chloro-4-methoxy-[1,2,4]triazolo[4,3-a]quinoxaline, m.p. 250°–252° C.

(f) Preparation of 7-chloro-4-hydroxy-[1,2,4]triazolo[4,3-a]quinoxaline

A mixture consisting of 3.4 g. (0.014 mole) of 7-chloro-4-methoxy-[1,2,4]triazolo[4,3-a]quinoxaline, 35 ml. of 1N hydrochloric acid and 105 ml. of glacial acetic acid was refluxed for a period of 2.5 hours. Upon completion of this step, the reaction mixture was cooled to room temperature and poured over ice/water. The resulting mixture was then stirred for a period of 20 minutes, filtered and the recovered solid product washed with water and air-dried to constant weight to ultimately afford 2.6 g. (87%) of pure 7-chloro-4-hydroxy-[1,2,4]triazolo[4,3-a]quinoxaline, m.p. >300° C.

(g) Preparation of 4,7-dichloro-[1,2,4]triazolo[4,3-a]quinoxaline

In a flame-dried reaction flask under a dry nitrogen atmosphere, there were placed 2.6 g. (0.012 mole) of 7-chloro-4-hydroxy-[1,2,4]-triazolo[4,3-a]quinoxaline and 40 ml. of phosphorus oxychloride together with 2.6 ml. of tri-n-propylamine. The reaction mixture was then refluxed overnight for approximately 16 hours and finally cooled to room temperature prior to being slowly poured over ice/water. The resulting aqueous mixture was next extracted with ethyl acetate and the latter extract was successively washed with water, saturated aqueous sodium bicarbonate solution and saturated brine before being dried over anydrous magnesium sulfate. After removal of the drying agent by means of filtration and the solvent by means of evaporation under reduced pressure, there was ultimately obtained a yellowish solid product as residue which was subsequently chromatographed on a 200 ml. silica gel column and then eluted with chloroform/methanol (9:1 by volume). Like fractions were then combined and concentrated in vacuo to finally afford an orange solid product which consisted of 1.89 g. (66%) of pure 4,7-dichloro-[1,2,4]triazolo[4,3-a]quinoxaline, m.p. 253°–256° C. (decomp.). Mass Spectrum: m/e, 238 (P); m/e, 240 (P+2); m/e, 242 (P+4).

PREPARATION D 4,7-Dichloro-1-ethyl-[1,2,4]triazolo[4,3-a]quinoxaline

(a) Preparation of 7-chloro-1-ethyl-4-methoxy-[1,2,4]triazolo-[4,3-a]quinoxaline A mixture consisting of 5.1 g. (0.022 mole) of 6-chloro-2-hydrazino-3-methoxyquinoxaline, the product of Preparation C(d), and 60 ml. of triethyl orthopropionate was heated with mechanical stirring in a preheated oil bath at 100° C. overnight ($\sim$16 hours). The resulting mixture was then cooled to room temperature ($\sim$20° C.), and the precipitate which formed was subsequently collected by means of suction filtration and washed with diethyl ether to ultimately afford 4.3 g. (75%) of pure 7-chloro-1-ethyl-4-methoxy-[1,2,4]triazolo[4,3-a]quinoxaline, m.p. 221°–223° C.

(b) Preparation of 7-chloro-1-ethyl-4-hydroxy-[1,2,4]triazolo[4,3-a]quinoxaline A mixture consisting of 4.3 g. (0.0072 mole) of 7-chloro-1-ethyl-4-hydroxy-[1,2,4]triazolo[4,3-a]quinoxaline, 40 ml. of 1N hydrochloric acid and 60 ml. of methanol was refluxed overnight and then cooled to room temperature. The precipitate which formed was subsequently collected by means of suction filtration and washed with methanol. In this manner, there were ultimately obtained 3.7 g. (94%) of pure 7-chloro-1-ethyl-4-hydroxy-[1,2,4]triazolo[4,3-a]quinoxaline, m.p. >300° C.

(c) Preparation of 4,7-dichloro-1-ethyl-[1,2,4]triazolo[4,3-a]quinoxaline

In a flame-dried reaction flask under a dry nitrogen atmosphere, there were placed 5.1 g. (0.02 mole) of 7-chloro-1-ethyl-4-hydroxy-[1,2,4]triazolo[4,3-a]quinoxaline and 75 ml. of phosphorus oxychloride together with 5 ml. of tri-n-propylamine. The reaction mixture was then refluxed overnight for approximately 16 hours and finally cooled to room temperature prior to being slowly poured over ice/water. The resulting aqueous mixture was next stirred at room temperature for 15 minutes and filtered, and the solid product so obtained was subsequently washed with cold water and air-dried to constant weight to ultimately afford 4.2 g. (79%) of pure 4,7-dichloro-1-ethyl-[1,2,4]triazolo[4,3-a]quinoxaline, m.p. 217°–220° C. (decomp.). Mass Spectrum: m/e, 266 (P); m/e, 268 (P+2); m/e, 265 (P−1).

PREPARATION E

4-Chloro-7-methoxy-[1,2,4]triazolo[4,3-a]quinoxaline (a) Preparation of 2,3-dihydroxy-6-methoxyquinoxaline A mixture consisting of 20 g. (0.114 mole) of 4-methoxy-o-phenylenediamine and 11 g. (0.114 mole) of triethylamine dissolved in 200 ml. of diethyl oxalate was refluxed overnight for a period of approximately 16 hours. Upon completion of this step, the reaction mixture was cooled to room temperature ($\sim$20° C.) and filtered to remove the desired product. After washing with ethanol, there were ultimately obtained 14.8 g. (68%) of pure 2,3-dihydroxy-6-methoxyquinoxaline, m.p. >300° C. Mass Spectrum: m/e, 192 (P).

(b) Preparation of 2,3-dichloro-6-methoxyquinoxaline

In a flame-dried reaction flask under a dry nitrogen atmosphere, there were placed 14.8 g. (0.077 mole) of 2,3-dihydroxy-6-methoxyquinoxaline and 75 ml. of phosphorus oxychloride together with 15 ml. of tri-n-propylamine. The exothermic reaction mixture was then allowed to stir at room temperature (~20° C.) for a period of one hour and thereafter was refluxed overnight (~16 hours). Upon completion of this step, the reaction mixture was again cooled to room temperature and finally poured slowly over ice/water. The resulting aqueous mixture was then stirred at room temperature for a period of 20 minutes, filtered and the recovered precipitate washed with water prior to being dissolved in chloroform. The latter solution was then filtered to remove insoluble material and the filtrate so obtained was successively washed with water, saturated sodium bicarbonate solution and saturated brine. Concentration of the washed solution in vacuo, followed by recrystallization of the residue from ethanol, then gave 14.2 g. (80%) of pure 2,3-dichloro-6-methoxyquinoxaline, m.p. 156°-159° C. Mass Spectrum: m/e, 228 (P); m/e, 230 (P+2); m/e, 232 (p+4).

(c) Preparation of 2-chloro-3,6-dimethoxyquinoxaline

In a flame-dri ed reaction flask under a dry nitrogen atmosphere, there was slowly added a solution consisting of 850 mg. of sodium dissolved in 80 ml. of methanol to a slurry of 7.1 g. of 2,3-dichloro-6-methoxyquinoxaline in 60 ml. of methanol at 50° C. over a period of seven hours. The resulting mixture was then heated at 50° C. overnight and finally cooled to room temperature. Upon completion of this step, the spent reaction mixture was concentrated in vacuo and the residue subsequently dissolved in chloroform, followed by washing with water and drying over anhydrous magnesium sulfate. After removal of the drying agent by means of filtration and the solvent by means of evaporation under reduced pressure, the resulting resiuue was subsequently chromatographed on a column of 400 ml. of silica gel, followed by elution with toluene. The good fractions were combined and concentrated in vacuo to ultimately afford a white solid consisting of 6.1 g (88%) of pure 2-chloro-3,6-methoxyquinoxaline m.p. 79°-81° C.

Anal. Calcd. for $C_{10}H_9ClN_2O_2$: C, 53.47; H, 4.04; N, 12.47. Found: C, 53.29; H, 4.05; N, 12.28.

(d) Preparation of 3,6-dimethoxy-2-hydrazinoquinoxaline

A mixture consisting of 5 g. (0.022 mole) of 2-chloro-3,6-dimethoxyquinoxaline and 2.8 g. (0.056 mole) of hydrazine hydrate (2.7 ml.) in 75 ml. of ethanol was heated at 50° C. overnight. Upon completion of this step, a further 1.0 ml. of hydrazine hydrate was added to the mixture and the resulting mixture was heated at 50° C. for a period of six hours. At this point, another 1.0 ml. of hydrazine hydrate was added and the final reaction mixture was heated at 50° C. overnight prior to being cooled to room temperature. The spent mixture was then filtered and the recovered precipitate washed with ethanol to ultimately afford 4.1 g. (85%) of pure 3,6-dimethoxy-2-hydrazinoquinoxaline, m.p. 128°-130° C. (decomp.).

(e) Preparation of 4,7-dimethoxy-[1,2,4]triazolo[4,3-a]quinoxaline

A mixture consisting of 1.5 g. (0.068 mole) of 3,6-dimethoxy-2-hydrazinoquinoxaline and 20 ml. of triethylorthoformate was heated with mechanical stirring in a preheated oil bath at 100° C. overnight (~16 hours). The resulting mixture was then cooled to room temperature, and the precipitate which formed was subsequently recovered by means of suction filtration and washed with ethanol to ultimately afford 1.8 g. of pure 4,7-dimethoxy-[1,2,4]triazolo[4,3-a]quinoxaline, m.p. 238°-240° C. (decomp.). Mass Spectrum: m/e, 230 (P); m/e, 231 (P+1); m/e, 232 (P+2).

(f) Preparation of 4-hydroxy-7-methoxy-[1,2,4]triazolo[4,3-a]quinoxaline

A mixture consisting of 1.6 g. (0.0069 mole) of 4,7-dimethoxy-[1,2,4]4]triazolo[4,3-a]quinoxaline, 16 ml. of 1N hydrochloric acid and 48 ml. of glacial acetic acid was refluxed for a period of three hours. Upon completion of this step, the reaction mixture was poured over ice and filtered. The recovered product was then collected on the filter funnel and washed with diethyl ether to ultimately afford 1.19 g. (80%) of pure 4-hydroxy-7-methoxy-[1,2,4]triazolo[4,3-a]quinoxaline, m.p. >250° C.

(g) Preparation of 4-chloro-7-methoxy-[1,2,4]triazolo[4,3-a]quinoxaline

In a flame-dried reaction flask under a dry nitrogen atmosphere, there were placed 1.1 g. (0.0055 mole) of 4-hydroxy-7-methoxy-[1,2,4]triazolo[4,3-a]quinoxaline and 15 ml. of phosphorus oxychloride together with 1.0 ml. of tri-n-propylamine. The reaction mixture was then refluxed overnight for approximately 16 hours and finally cooled to room temperature prior to being slowly poured over ice/water. The resulting aqueous mixture was next extracted with ethyl acetate, and the latter extract was successively washed with water and saturated brine before being dried over anhydrous magnesium sulfate. After removal of the drying agent by means of filtration and the solvent by means of evaporation under reduced pressure, there was ultimately obtained a residual product that was subsequently chromatographed on a 150 ml. silica gel column and then eluted with chloroform/methanol (95:5 by volume). Like fractions containing the product were then combined and concentrated in vacuo to finally afford a residual material, which was recrystallized from chloroform/diethyl ether to yield 400 mg. (31%) of pure 4-chloro-7-methoxy-[1,2,4]triazolo[4,3-a]quinoxaline, m.p. 266°-268° C. (decomp.). Mass Spectrum: m/e, 234 (P); m/e, 236 (P+2).

PREPARATION F

4-Chloro-1-ethyl-7-methoxy-[1,2,4]triazolo[4,3-a]quinoxaline (a) Preparation of 1-ethyl-4,7-dimethoxy-[1,2,4]triazolo[4,3-a]quinoxaline A mixture consisting of 4.0 g. (0.018 mole) of 3,6-dimethoxy-2-hydrazinoquinoxaline, the product of Preparation E(d), and 50 ml. of triethyl orthopropionate was heated with mechanical stirring in a preheated oil bath at 100° C. overnight (~16 hours). The resulting reaction mixture was then cooled to room temperature (~20° C.), and the precipitate which formed was subsequently recovered by means of suction filtration and washed with ethanol to ultimately afford 3.3 g. (72%) of pure 4,7-dimethoxy-1-ethyl-[1,2,4]triazolo[4,3-a]quinoxaline, m.p. 184°–188° C. Mass Spectrum: m/e, 258 (P); m/e, 228 (P−30).

(b) Preparation of 1-ethyl-4-hydroxy-7-methoxy-[1,2,4]triazolo[4,3-a]quinoxaline A mixture consisting of 3.3 g. (0.013 mole) of 4,7-dimethoxy-1-ethyl-[1,2,4]triazolo[4,3-a]quinoxaline, 33 ml. of 1N hydrochloric acid and 99 ml. of glacial acetic acid was refluxed for a period of two hours. Upon completion of this step, the reaction mixture was cooled to room temperature and poured over ice/water. The resulting mixture was then stirred for a period of 20 minutes and extracted with ethyl acetate. The latter extract next washed with saturated brine and dried over anhydrous magnisium sulfate. After removal of the drying agent by means of filtration and the solvent by means of evaporation under reduced pressure, there was finally obtained a yellowish solid product which was washed with water and air-dried to constant weight to ultimately afford 1.87 g. (67%) of pure 1-ethyl-4-hydroxy-7-methoxy-[1,2,4]triazolo[4,3-a]quinoxaline, m.p. >250° C.

(c) Preparation of 4-chloro-1-ethyl-7-methoxy-[1,2,4]triazolo[4,3-a]-quinoxaline In a flame-dried reaction flask under a dry nitrogen atmosphere, there were placed 1.87 g. (0.0076 mole) of 1-ethyl-4-hydroxy-7-methoxy-[1,2,4]triazolo[4,3-a]quinoxaline and 25 ml. of phosphorus oxychloride together with 1.8 ml. of tri-n-propylamine. The reaction mixture was then refluxed overnight for approximately 16 hours and finally cooled to room temperature prior to being slowly poured over ice/water. The resulting aqueous mixture was then stirred at room temperature for 30 minutes and filtered, and the solid product so obtained was subsequently washed with cold water and then dissolved in chloroform. The latter organic solution was thereafter washed with saturated brine and dried over anhydrous magnesium sulfate. After removal of the drying agent by means of filtration and the solvent by means of evaporation under reduced pressure, there was finally obtained a yellow solid product which was triturated with diethyl ether and filtered to ultimately afford 1.6 g. (80%) of pure 4-chloro-1-ethyl-7-methoxy-[1,2,4]triazolo[4,3-a]quinoxaline, m.p. 173°–175° C. Mass Spectrum: m/e, 262 (P); m/e, 264 (P+2); m/e, 261 (P−1).

PREPARATION G

4-Chloro-8-fluoro-[1,2,4]triazolo[4,3-a]quinoxaline (a) Preparation of 2,3-dihydroxy-6-fluoroquinoxaline A mixture consisting of 26.3 g. (0.19 mole) of 4-fluoro-1,2-phenylenediamine [*Journal of the American Chemical Society*, Vol. 75, P. 1294 (1953)] and 150 ml. of diethyl oxalate was refluxed under a nitrogen atmosphere for a period of 18 hours. Upon completion of this step, the reaction mixture was cooled to room temperature (~20° C.), filtered and the recovered product subsequently washed with four-100 ml. portions of ethanol and air-dried to constant weight to ultimately afford 19.3 g. (80%) of pure 2,3-dihydroxy-6-fluoroquinoxaline, m.p. >300° C. (literature m.p. 387°–390° C., according to U.S. Pat. No. 3,992,378). Mass Spectrum: m/e, 180 (P+).

(b) Preparation of 2,3-dichloro-6-fluoroquinoxaline

A mixture consisting of 19 g. (0.105 mole of 2,3-dihydroxy-6-fluoroquinoxaline and 50 ml. of phosphorus oxychloride was refluxed overnight (~16 hours) and then cooled to room temperature prior to being poured over 200 g. of ice with good stirring. The resulting aqueous mixture was then filtered, and the recovered product subsequently washed several times with water to ultimately afford 28.2 g. of 2,3-dichloro-6-fluoroquinoxaline, m.p. 148°–152° C.

(c) Preparation of 2-chloro-6-fluoro-3-hydrazinoquinoxaline

To a suspension of 28.2 g. (0.105 mole) of 2,3-dichloro-6-fluoroquinoxaline in 500 ml. of ethanol, there were added 1 ml. (0.31 mole) of hydrazine hydrate over a period of two minutes to give a dark red suspension. The resulting mixture was then stirred under a nitrogen atmosphere at room temperature for a period of 20 hours. At this point, the precipitate was filtered and washed several times with ethanol, followed by air-drying to constant weight to ultimately afford 20.7 g. (93%) of pure 2-chloro-6-fluoro-3-hydrazinoquinoxaline, m.p. 190°–192° C. (decomp.).

(d) Preparation of 4-chloro-8-fluoro-[1,2,4]triazolo[4,3-a]quinoxaline

A mixture consisting of 10 g. (0.047 mole) of 2-chloro-6-fluoro-3-hydrazinoquinoxaline and 80 ml. (0.47 mole) of triethyl orthoformate was heated under a nitrogen atmosphere with mechanical stirring in a preheated oil bath at 100° C. overnight (~16 hours). The resulting mixture was cooled to room temperature, and the precipitate which formed was subsequently recovered by means of suction filtration, washed with three-50 ml. portions of ethanol and air-dried to constant weight to ultimately afford 9.42 g. (91%) of pure 4-chloro-8-fluoro-[1,2,4]triazolo[4,3-a]quinoxaline, m.p. 310°–312° C. (decomp.). Mass Spectrum: m/e, 224, 223, 222 (P+).

PREPARATION H

4-Chloro-1-ethyl-8-fluoro-[1,2,4]triazolo[4,3-a]quinoxaline

A mixture consisting of 10.0 g. (0.047 mole) of 2-chloro-6-fluoro-3-hydrazinoquinoxaline, the product of Preparation G(c), and 95 ml. (0.47 mole) of triethyl orthpropionate was heated under a nitrogen atmosphere with mechanical stirring in a preheated oil bath at 100° C. overnight (~16 hours). The resulting mixture was cooled to room temperature (~20° C.), and the precipitate which formed was subsequently recovered by means of suction filtration, washed with three 50 ml. portions of ethanol and air-dried to constant weight to ultimately afford 7.5 g. (65%) of pure 4-chloro-1-ethyl-8-fluoro-[1,2,4]triazolo[4,3-a]quinoxaline, m.p. 160°–163° C. (decomp.). Mass Spectrum: m/e, 249, 250, 251, 252 (P+).

PREPARATION I

4-Chloro-8-fluoro-1-trifluoromethyl-[1,2,4]triazolo[4,3-a]quinoxaline (a) Preparation of 8-fluoro-4-hydroxy-1-trifluoromethyl-[1,2,4]triazolo[4,3-a]quinoxaline A mixture consisting of 12.8 g. (0.06 mole) of 2-chloro-6-fluoro-3-hydrazinoquinoxaline in 50 ml. (0.65 mole) of trifluoracetic acid was heated under a dry nitrogen atmosphere at 120° C. for a period of 24 hours with the aid of mechanical stirring to give a homogeneous solution. The resulting reaction mixture was then poured with stirring over ice/water, stirred for an additional 30 minutes and filtered. The product so obtained was thereafter washed with three-separate portions of water and dried in vacuo at 80° C. to ultimately afford 12.58 g. (77%) of pure 8-fluoro-4-hydroxy-1-trifluoromethyl-[1,2,4]triazolo[4,3-a]quinoxaline, m.p. 298°–302° C. Mass Spectrum: m/e, 272 (P+).

(b) Preparation of 4-chloro-8-fluoro-1-trifluoromethyl-[1,2,4]triazolo[4,3-a]quinoxaline In a flame-dried 250 ml. three-necked reaction flask under a dry nitrogen atmosphere, there were placed 12.5 g. (0.046 mole) of 8-fluoro-4-hydroxy-1-trifluoromethyl-[1,2,4]triazolo[4,3-a]quinoxaline and 85 ml. of phosphorus oxychloride together with 17.5 ml. of tri-n-propylamine. The reaction mixture was then refluxed overnight for approximately 16 hours and finally cooled to room temperature (~20° C.) prior to being slowly poured over 1000 ml. of ice/water with the aid of mechanical stirring. The resulting aqueous mixture was next stirred for an additional period of 30 minutes at room temperature, followed by extraction with three-300 ml. portions of chloroform. The combined chloroform layers were then successively washed with saturated aqueous sodium bicarbonate solution, water and saturated brine and finally dried over anhydrous magnesium sulfate. After removal of the drying agent by means of filtration and the solvent by means of evaporation under reduced pressure, there was finally obtained a yellow solid product which consisted of 10.47 g. (79%) of pure 4-chloro-8-fluoro-1-trifluoromethyl-[1,2,4]triazolo[4,3-a]quinoxaline, m.p. 135°–138° C. Mass Spectrum: m/e, 292/290 (P+).

PREPARATION J

4-Chloro-7,8-difluoro-[1,2,4]triazolo[4,3-a]quinoxaline (a) Preparation of 2,3-dihydroxy-6,7-difluoroquinoxaline A mixture consisting of 11.3 g. (0.0784 mole) of 4,5-difluoro-o-phenylenediamine (U.S. Pat. No. 4,264,600) and 80 ml. (0.589 mole) of diethyl oxalate was refluxed for a period of four hours to give a thick precipitate of product. The spent reaction mixture was then cooled to room temperature (~20° C.) overnight, filtered and the solid product so obtained was thereafter washed several times with diethyl ether and air-dried to constant weight to ultimately afford 15.5 g of pure 2,3-dihydroxy-6,7-difluoroquinoxaline, m.p. >310° C.. Mass Spectrum: m/e, 198 (P+).

(b) Preparation of 2,3-dichloro-6,7-difluoroquinoxaline

A mixture consisting of 15.4 g. (0.078 mole) of 2,3-dihydroxy-6,7-difluoroquinoxaline, 39 g. (0.187 mole) of phosphorus pentachloride and 20 ml. (0.22 mole) of phosphorus oxychloride was refluxed with stirring for a period of four hours, during which time an additional amount of 20 ml. of phosphorus oxychloride was added to facilitate the stirring (the reaction mixture become homogeneous within 30 minutes). Upon completion of this step, the reaction mixture was stirred overnight (~16 hours) at room temperature to give a light yellow precipitate. The spent mixture was then poured over 200 g. of ice/water and further stirred with additional cooling to give a tan solid which consisted of 20.9 g of 2,3-dichloro-6,7-difluororquinoxaline, m.p. 162°–164° C. (decomp.). Mass Spectrum: m/e, 238/236/234 (P+).

(c) Preparation of 2-chloro-6,7-difluoro-3-hydrazinoquinoxaline

A mixture consisting of 10 g. (0.0426 mole) of 2,3-dichloro-6,7-difluoroquinoxaline and 5 ml. (0.03 mole) of hydrazine hydrate in 200 ml. of ethanol was stirred at room temperature for a period of 24 hours to give a rust-red precipitate. The thick slurry was filtered and the recovered product washed with two-20 ml. portions of ethanol, followed by air-drying to constant weight to ultimately afford 5.99 g. (67%) of pure 2-chloro-6,7-difluoro-3-hydrazinoquinoxaline, m.p. 212°–215° C. (decomp.). Mass Spectrum: m/e, 230 (P); m/e, 232 (P+).

(d) Preparation of 4-chloro-7,8-difluoro-[1,2,4]triazolo[4,3-a]quinoxaline

A mixture consisting of 5.99 g. (0.026 mole) of 2-chloro-6,7-difluoro-3-hydrazinoquinoxaline and 30 ml. (0.18 mole) of triethyl orthoformate was heated at 100° C. for a period of 24 hours to give a red-brown solid. The resulting slurry was then cooled to room temperature and filtered, and the recovered product subsequently washed with diethyl ether to ultimately afford 5.15 g. (82%) of pure 4-chloro-7,8-difluoro-[1,2,4]triazolo[4,3-a]quinoxaline, m.p. >210° C. (decomp.). Mass Spectrum: m/e, 242/240 (P+).

PREPARATION K

4-Chloro-6,7-difluoro-1-ethyl-[1,2,4]triazolo[4,3-a]quinoxaline

A mixture consisting of 7.0 g. (0.03 mole) of 2-chloro-6,7-difluoro-3-hydrazinoquinoxaline, the product of Preparation J(c), and 60 ml. (0.30 mole) of triethyl orthopropionate was heated under a nitrogen atmosphere with mechanical stirring in a preheated oil bath at 100° C. for a period of 24 hours. The resulting mixture was cooled to room temperature (~20° C.), and the red precipitate which formed was subsequently recovered by means of suction filtration, washed with two separate portions of diethyl ether and air-dried to constant weight to ultimately afford 4.15 g (52%) of pure 4-chloro-6,7-difluoro-1-ethyl-[1,2,4]triazolo[4,3-a]quinoxaline, m.p. 185°–186° C. (decomp.).

PREPARATION L 4,8-Dichloro-1-methyl-[1,2,4]triazolo[4,3-a]quinoxaline (a) Preparation of 2,6-dichloro-6-hydrazinoquinoxaline A mixture consisting of 23 g. (0.10 mole) of 2,3,6-trichloroquinoxaline and 11 g. (0.22 mole) of hydrazine hydrate in 500 ml. of ethanol was stirred at room temperature (~20° C.) overnight (~16 hours). The precipitate which formed was separated by filtration and washed with ethanol to ultimately afford 22.2 g. (97%) of pure 2,6-dichloro-3-hydrazinoquinoxaline, m.p. <250° C. Mass Spectrum: m/e, 228 (P).

(b) Preparation of 4,8-dichloro-1-methyl-[1,2,4]triazolo[4,3-a]quinoxaline

A mixture consisting of 20 g. (0.087 mole) of 2,6-dichloro-3-hydrazinoquinoxaline and 160 ml. (0.87 mole) of triethyl orthoacetate was heated with mechanical stirring under a dry nitrogen atmosphere in a preheated oil bath at 100° C. for a period of 20 hours to give a yellow suspension. The resulting mixture was cooled to room temperature and filtered, and the recovered solid product was subsequently washed with ethanol and air-dried to constant weight to ultimately afford 10.2 g. (46%) of pure 4,8-dichloro-1-methyl-[1,2,4]triazolo[4,3-a]quinoxaline, m.p. >280° C. Mass Spectrum: m/e, 254/252 (P+).

PREPARATION M 4,8-Dichloro-1-trifluoromethyl-[1,2,4]triazolo[4,3-a]quinoxaline (a) Preparation of 8-chloro-4-hydroxy-1-trifluoromethyl-[1,2,4]triazolo[4,3-a]quinoxaline In a flame-dried 500 ml. three-necked reaction flask equipped with mechanical stirrer, nitrogen-inlet tube and reflux condenser, there were placed 67 ml. (0.87 mole) of trifluoroacetic acid. Stirring was commenced and 20 g. (0.087 mole) of 2,6-dichloro-3-hydrazinoquinoxaline, the product of Preparation L(a) were added thereto. The resulting reaction mixture was then heated on a steam bath for a period of 24 hours, cooled to room temperature (~20° C.) and poured over 200 g. of ice/water. The aqueous mixture so obtained was then stirred for 30 minutes, filtered and the recovered product subsequently washed several times with water and air-dried to constant weight (required approximately 18 hours). In this way, there were ultimately obtained 14.3 g. (57%) of pure 8-chloro-4-hydroxy-1-trifluoromethyl-[1,2,4]triazolo[4,3-a]quinoxaline, m.p. 253°–255° C. (decomp.) Mass Spectrum: m/e, 290/288 (P+).

(b) Preparation of 4,8-dichloro-1-trifluoromethyl-[1,2,4]triazolo[4,3-a]quinoxaline In a flame-dried 250 ml. three-necked reaction flask equipped with mechanical stirrer, dropping funnel and reflux condenser, under a nitrogen sweep, there were placed 14.3 g. (0.05 mole) of 8-chloro-4-hydroxy-1-trifluoromethyl-[1,2,4]triazolo[4,3-a]quinoxaline in 100 ml. of phosphorus oxychloride. To the resulting suspension, there were then added in a dropwise manner 19 ml. (0.10 mole) of tri-n-propylamine over a period of five minutes. The resulting reaction mixture was then refluxed for a period of 20 hours to give a clear dark wine-red solution. Upon completion of this step, the clear solution so obtained was cooled to room temperature and poured over 1000 ml. of ice/water with the aid of strong mechanical stirring. The resulting aqueous mixture was then stirred at room temperature for a period of 30 minutes and next extracted with three-500 ml. portion of chloroform. The latter organic extracts were subsequently combined and then successively washed with water, saturated aqueous sodium bicarbonate solution, water and saturated brine, followed by drying over anhydrous magnesium sulfate. After removal of the drying agent by means of filtration and the solvent by means of evaporation under reduced pressure, there was finally obtained a yellow solid which consisted of 11.4 g. (75%) of pure 4,8-dichloro-1-trifluoromethyl-[1,2,4]triazolo[4,3-a]quinoxaline, m.p. 133°–135° C. Mass Spectrum: m/e, 308 (P+2); m/e, 310 (P+4).

PREPARATION N 4,8-Dichloro-1-phenyl-[1,2,4]triazolo[4,3-a]quinoxaline

In a 250 ml. three-necked reaction flask equipped with mechanical stirrer and reflux condenser, there were placed 50.0 g. (0.274 mole) of trimethyl orthobenzoate that had been preheated to ca. 70° C. Stirring was commenced and 10.0 g (0.0437 mole) of 2,6-dichloro-3-hydrazinoquinoxaline, the product of Preparation L(a), were added thereto. The resulting reaction mixture was then heated at ca. 120° C., with continued stirring, for a period of 24 hours, followed by cooling to room temperature (~20° C.) and stirring overnight for approximately 16 hours to give a yellow slurry. The latter slurry was then filtered, and the recovered solid product was subsequently washed with two-50 ml. portions of ethanol and air-dried to constant weight to ultimately afford 9.8 g. (72%) of crude 4,8-dichloro-1-phenyl-[1,2,4]triazolo[4,3-a]quinoxaline, m.p. 305°–307° C. Mass Spectrum: m/e, 316/314 (P+).

EXAMPLE 1

2-Chloro-3-hydrazinoquinoxaline 2,3-Dichloroquinoxaline (33.5 g., 0.168 mole) was stirred with hydrazine hydrate (18.5 g., 0.369 mole) in 500 ml. of ethanol at room temperature overnight (i.e.. at ca. 20° C. for approximately 16 hours). The thick, yellow slurry was filtered and the precipitate was washed with ethanol. The precipitated material was recrystallized from hot methanol to give 13.5 g. (41% yield) of 2-chloro-3-hydrazinoquinoxaline, m.p. 181° C. (decomp.). Mass spectrum: m/e, 194 (P).

EXAMPLE 2

4-Chloro-[1,2,4]triazolo[4,3-a]quinoxaline

2-Chloro-3-hydrazinoquinoxaline (9.0 g., 0.046 mole) the product of Example 1, was stirred with triethyl orthoformate (90 ml.) at 100° C. for one hour. The mixture was cooled to room temperature and the solid precipitate was collected by filtration and washed with cyclohexane and dried to afford 8.8 g. (94% yield) of 4-chloro-[1,2,4]triazolo[4,3-a]quinoxaline, m.p. 287°–290° C. (decomp.). Mass spectrum: m/e, 204 (P).

EXAMPLE 3

4-Chloro-1-methyl-[1,2,4]triazolo[4,3-a]quinoxaline

2-Chloro-3-hydrazinoquinoxaline (15.5 g., 0.080 mole), the product of Example 1, was stirred with triethyl orthoacetate for 3 hours at 100° C. The mixture was cooled to room temperature and the solid precipitate was collected by filtration, washed with ethanol and air dried to afford 11.4 g. (65% yield) of 4-chloro-1-methyl-[1,2,4]triazolo[4,3-a]quinoxaline, m.p. 215°–222° C. Mass spectrum: m/e, 218 (P).

EXAMPLE 4

4-Chloro-1-ethyl-[1,2,4]triazolo[4,3-a]quinoxaline

2-Chloro-3-hydrazinoquinoxaline (4.5 g., 0.023 mole) the product of Example 1, was stirred with triethyl orthopropionate (50 ml.) at 100° C. for one hour. The mixture was cooled to room temperature and the white precipitate was collected by filtration and washed with cyclohexane to give 4.5 g. (85% yield) of 4-chloro-1-ethyl-[1,2,4]triazolo[4,3-a]quinoxaline, m.p. 158°–160° C. Mass spectrum: m/e, 232 (P).

EXAMPLE 5

4-Chloro-1-n-propyl-[1,2,4]triazolo[4,3-a]quinoxaline

2-Chloro-3-hydrazinoquinoxaline (3.0 g., 0.015 mole), the product of Example 1, was stirred with triethyl orthobutyrate (27 ml.) at 100° C. for 2 hours. The mixture was cooled to room temperature, and the precipitate was collected by filtration and washed with cyclohexane. The crude solid was taken up in chloroform and filtered to remove insoluble material. The chloroform solution was concentrated in vacuo to give a solid which was recrystallized from chloroform to give 1.96 g. (53% yield) of 4-chloro-1-n-propyl-[1,2,4]triazolo[4,3-a]quinoxaline, m.p. 173°–175° C. Mass spectrum: m/e, 246 (P).

EXAMPLE 6

4-Chloro-1-isopropyl-[1,2,4]triazolo[4,3a]quinoxaline

2-Chloro-3-hydrazinoquinoxaline (4.0 g., 0.02 mole), the product of Example 1, was stirred with triethyl orthoisobutyrate (15 ml.) at 100° C. for three hours. The solution was cooled to room temperature and the precipitate was collected by filtration and washed with ethanol. The crude solid was recrystallized from 300 ml. of hot ethanol to afford 2.06 g. (40% yield) of 4-chloro-1-isopropyl-[1,2,4]triazolo[4,3a]quinoxaline, m.p. 208°–210° C. Mass spectrum: m/e, 246 (P).

EXAMPLE 7

4-Methylamino-[1,2,4]triazolo[4,3-a]quinoxaline

4-Chloro-[1,2,4]triazolo-[4,3-a]quinoxaline (2.0 g., 0.01 mole), the product of Example 2, in N,N-dimethyl formamide (30 ml.) was saturated with monomethylamine gas and stirred at room temperature for 3 hours. Monomethylamine gas was again bubbled into the solution and the solution was stirred at room temperature for an additional 2 hours. The precipitate was separated by filtration and washed with N,N-dimethylformamide. Recrystallization from N,N-dimethylformamide gave 1.37 g. (69% yield) of 4-methylamino-[1,2,4]triazolo[4,3-a]quinoxaline, m.p. >300° C. Mass spectrum: m/e, 199 (P).

Anal. Calcd. for $C_{10}H_9N_5$: C, 60,29; H, 4.55; N, 35.15.
Found: C, 59.99; H, 4.47; N, 35.11.

EXAMPLE 8

4-Dimethylamino-[1,2,4]triazolo[4,3-a]quinoxaline

A slurry of 2.0 g. (0.01 mole) of 4-chloro-[1,2,4]triazolo[4,3-a]quinoxaline (the product of Example 2) in N,N-dimethylformamide (30 ml.) was saturated with dimethylamine gas and stirred at room temperature overnight. The mixture was poured over ice and the precipitate was removed by filtration. Recrystallization from ethanol gave 640 mg. (44% yield) of 4-dimethylamino-[1,2,4]triazolo[4,3-a]quinoxaline, m.p. 184°–186° C. Mass spectrum: m/e, 213 (P).

Anal. Calcd. for $C_{11}H_{11}N_5$: C, 61.96; H, 5.20; N, 32.84.
Found: C, 62.26; H, 5.43; N, 32.92.

EXAMPLE 9

4-Ethylamino-[1,2,4]triazolo[4,3-a]quinoxaline

A slurry of 2.0 g. (0.01 mole) of 4-chloro-[1,2,4]triazolo[4,3-a]quinoxaline (the product of Example 2) in N,N-dimethylformamide (30 ml.) was saturated with monoethylamine gas and stirred at room temperature for 2 hours. Monoethylamine gas was again bubbled through the mixture and stirring was continued for 2 hours. The precipitate was removed by filtration and washed with N,N-dimethylformamide. Recrystallization from methanol afforded 680 mg. (32% yield) 4-ethylamino-[1,2,4]triazolo[4,3-a]quinoxaline, m.p. 254°–256° C. Mass spectrum: m/e, 213 (P).

Anal. Calcd. for $C_{11}H_{11}N_5$: C, 61.96; H, 5.20; N, 32.84.
Found: C, 61.93; H, 5.09; N, 32.72.

EXAMPLE 10

4-Diethylamino-[1,2,4]triazolo[4,3-a]quinoxaline

4-Chloro-[1,2,4]triazolo[4,3-a]-quinoxaline (4.4 g., 0.021 mole), the product of Example 2, was stirred with diethylamine (6.5 ml., 0.063 mole) in N,N-dimethylformamide (100 ml.) at room temperature for 2 hours. The reaction mixture was poured over an ice-water mixture to form a crude precipitate as product, which was subsequently filtered and washed with water. Recrystallization from isopropanol gave 3.36 g. (66% yield) of 4-diethylamino-[1,2,4]triazolo[4,3-a]quinoxaline, m.p. 117°–119° C. Mass spectrum: m/e, 241 (P).

EXAMPLE 11

4-Di-n-propylamino-[1,2,4]triazolo[4,3a]quinoxaline

4-Chloro-[1,2,4]triazolo[4,3-a]-quinoxaline (2.0 g., 0.01 mole), the product of Example 2, and 3.0 g. (0.03 mole) of di-n-propylamine in N,N-dimethylformamide (50 ml.) were stirred for 3 hours at room temperature. The solution was poured over ice to form a precipitate which was separated by filtration and air dried. Recrystallization from cyclohexane (250 ml.) afforded 1.1 g. (41% yield) of 4-di-n-propylamino-[1,2,4]triazolo[4,3-a]quinoxaline, m.p. 240°–242° C. Mass spectrum: m/e, 269 (P).

Anal. Calcd. for $C_{15}H_{19}N_5$: C, 66.89; H, 7.11; N, 26.00.
Found: C, 66.68; H, 6.97; N, 26.12.

EXAMPLE 12

4-Isopropylamino-[1,2,4]triazolo[4,3-a]quinoxaline

4-Chloro-[1,2,4]triazolo[4,3-a]-quinoxaline (2.0 g., 0.01 mole), the product of Example 2, and 1.77 g. (0.03 mole) of isopropylamine in N,N-dimethylformamide (30 ml.) were stirred at room temperature overnight. The dark solution was poured over ice and the precipitate which was produced was separated by filtration and washed with water. The crude product was recrystallized from ethanol and then twice from isopropyl ether to afford 1.2 g. (53% yield) of 4-isopropylamino-[1,2,4]triazolo[4,3-a]quinoxaline, m.p. 133°–135° C. Mass spectrum: m/e, 222 (P).

Anal. Calcd. for $C_{12}H_{13}N_5 \cdot \frac{1}{3}H_2O$: C, 61.79; H, 5.90; N, 30.02.

Found: C, 61.51; H, 5.89; N, 29.90.

EXAMPLE 13

4-Diethylamino-1-methyl-[1,2,4]triazolo[4,3-a]quinoxaline

This compound was prepared by the method of Example 11, utilizing 4-chloro-1-methyl-[1,2,4]triazolo[4,3-a]quinoxaline (the product of Example 3) as starting material in place of 4-chloro-[1,2,4]triazolo[4,3-a]quinoxaline (the product of Example 2) and diethylamine as reagent in place of di-n-propylamine. The crude product obtained was recrystallized from chloroform and then from cyclohexane to afford 7.2 g. (54% yield) of pure 4-diethylamino-1-methyl-[1,2,4]triazolo[4,3-a]quinoxaline, m.p. 123°–125° C.

EXAMPLE 14

4-Amino-1-ethyl-[1,2,4]triazolo[4,3-a]quinoxaline

Ammonia gas was bubbled through a solution of 1.2 g. (0.005 mole) of 4-chloro-1-ethyl-[1,2,4]triazolo[4,3a]-quinoxaline (the product of Example 4) in N,N-dimethylformamide (20 ml.) at 0° C. for about 2 minutes. The solution was stirred at 0° C. for 30 minutes and at room temperature for one hour. The reaction mixture was then poured over ice and stirred for 20 minutes. The precipitate which formed was removed by filtration, washed with water and air dried. Recrystallization from ethanol afforded 220 mg. (22% yield) of pure 4-amino-1-ethyl-[1,2,4]triazolo[4,3-a]quinoxaline, m.p. 284°–288° C. Mass spectrum: m/e, 213 (P).

Anal. Calcd. for $C_{11}H_{11}N_5 \cdot 1/6H_2O$: C, 61.10; H, 5.28; N, 32.39. Found: C, 61.36; H, 5.14; N, 31.96.

EXAMPLE 15

4-Methylamino-1-ethyl-[1,2,4]triazolo[4,3-a]quinoxaline

Monomethylamine gas was bubbled through a solution of 4-chloro-1-ethyl-[1,2,4]triazolo[4,3-a]quinoxaline (1.2 g., 0.005 mole), the product of Example 4, in N,N-dimethylformamide (50 ml.) at 0° C. for 2 minutes. The reaction mixture was stirred at 0° C. for 30 minutes, at room temperature for 2 hours, and then poured over ice and stirred another 20 minutes. The precipitate which formed was separated by filtration, washed with water and air dried. Recrystallization from ethanol then afforded 1.0 g. (88% yield) of 4-methylamino-1-ethyl-[1,2,4]triazolo[4,3-a]quinoxaline, m.p. 271°–273° C. Mass spectrum: m/e, 227 (P).

Anal. Calcd. for $C_{12}H_{13}N_5 \cdot \frac{1}{3}H_2O$: C, 62.80; H, 5.82; N, 30.51.

Found: C, 62.72; H, 5.86; N, 30.62.

EXAMPLE 16

4-Dimethylamino-1-ethyl[1,2,4]triazolo[4,3-a]quinoxaline

4-Chloro-1-ethyl-[1,2,4]triazolo-[4,3-a]quinoxaline (1.2 g., 0.005 mole), the product of Example 4, and 676 mg. (0.015 mole) of anhydrous dimethylamine in N,N-dimethylformamide (50 ml.) were stirred at 0° C. for 30 minutes and at room temperature for 2 hours. The reaction mixture was poured over ice and stirred for 20 minutes. The precipitate which formed was separated by filtration, washed with water and air dried. Recrystallization from chloroform and then from chloroform/cyclohexane afforded 510 mg. (42% yield) of 4-dimethylamino-1-ethyl-[1,2,4]triazolo[4,3-a]quinoxaline, m.p. 155°–158° C. Mass spectrum: m/e, 241 (P).

Anal. Calcd. for $C_{13}H_{15}N_5$: C, 64.71; H, 6.27; N, 29.02.

Found: C, 64.69; H, 6.27; N, 29.32.

EXAMPLE 17

1-Ethyl-4-ethylamino-[1,2,4]triazolo[4,3-a]quinoxaline

Monoethylamine was bubbled through a solution of 4-chloro-1-ethyl-[1,2,4]triazolo[4,3-a]quinoxaline (1.2 g., 0.005 mole), the product of Example 4, in N,N-dimethylformamide (50 ml.) at 0° C. for about 2 minutes. The clear solution was stirred at 0° C. for 30 minutes and at room temperature for 2 hours. The reaction mixture was next poured over ice and the precipitate was separated by filtration, washed with water and air dried. Recrystallization from ethanol then afforded 1.0 g. (83% yield) of pure 1-ethyl-4-ethylamino-[1,2,4]triazolo[4,3-a]quinoxaline as a white solid (m.p. 235°–238° C.). Mass spectrum: m/e, 241 (P).

Anal. Calcd. for $C_{13}H_{15}N_5$: C, 64.71; H; 6.27; N; 29.02.

Found: C, 64.57; H, 6.20; N, 29.15.

EXAMPLE 18

4-Diethylamino-1-ethyl-[1,2,4]triazolo[4,3-a]quinoxaline

This compound was prepared by the method of Example 11, utilizing 4-chloro-1-ethyl-[1,2,4]triazolo[4,3-a]quinoxaline (the product of Example 4) as starting material in place of 4-chloro-[1,2,4]triazolo[4,3-a]quinoxaline (the product of Example 2) and diethylamine as reagent in place of di-n-propylamine. The crude product was recrystallized from cyclohexane to afford 3.54 g. (69% yield) of pure 4-diethylamino-1-ethyl-[1,2,4]triazolo[4,3-a]quinoxaline as a white solid (m.p. 98°–100° C.). Mass spectrum: m/e, 269 (P).

EXAMPLE 19

4-Isopropylamino-1-ethyl-[1,2,4]triazolo[4,3-a]quinoxaline

Isopropylamine (1.77 g., 0.03 mole) was added to a solution of 4-chloro-1-ethyl-[1,2,4]triazolo-[4,3-a]quinoxaline (2.3 g., 0.01 mole), the product of Example 4, in N,N-dimethylformamide (30 ml.). Within 30 minutes, a precipitate formed. The reaction mixture was then stirred overnight at room temperature. The precipitate was separated by filtration and washed with N,N-dimethylformamide. Recrystallization from ethanol then gave 1.6 g. (63% yield) of 4-isopropylamino-1-ethyl-[1,2,4]triazolo[4,3-a]quinoxaline, m.p. 222°–>4° C. Mass spectrum: m/e, 255 (P).

Anal. Calcd. for $C_{14}H_{17}N_5$: C, 65.86; H, 6.71; N, 27.43.

Found: C, 65.32; H, 6.76; N, 27.25.

EXAMPLE 20

4-Ethylamino-1-isopropyl-[1,2,4]triazolo[4,3-a]quinoxaline

A slurry of 1.0 g. (0.004 mole) of 4-chloro-1-isopropyl-[1,2,4]triazolo[4,3-a]quinoxaline (the product of Example 6) in N,N-dimethylformamide (15 ml.) was saturated with monoethylamine gas and stirred at room temperature for 4 hours. The precipitate was separated by filtration and washed with N,N-dimethylformamide to afford 220 mg. (22% yield) of 4-ethylamino-1-isopropyl-[1,2,4]triazolo[4,3-a]quinoxaline, m.p. 209°–211° C. Mass spectrum: m/e, 255 (P).

The filtrate was next poured over ice and the precipitate was separated by means of filtration, washed with water and recrystallized from methanol and then from isopropanol to afford another 200 mg. (20% yield) of pure 4-ethylamino-1-isopropyl-[1,2,4]triazolo[4,3-a]quinoxaline, m.p. 210°–211° C.

Anal. Calcd. for $C_{14}H_{17}N_5$: C, 65.86; H, 6.71; N, 27.43. Found: C, 65.53; H, 6.58; N, 27.29.

EXAMPLE 21
4-Diethylamino-1-isopropyl-[1,2,4]triazolo[4,3-a]quinoxaline

4-Chloro-1-isopropyl-[1,2,4]-triazolo[4,3-a]quinoxaline (1.0 g., 0.004 mole), the product of Example 6, and 900 mg. (0.012 mole) of diethylamine in N,N-dimethylformamide (15 ml.) were stirred at room temperature for 4 hours. The reaction mixture was poured over ice and the precipitate was separated by means of filtration, washed with water and placed on a column of silica gel (175 ml.) and finally eluted with chloroform. The eluant was evaporated in vacuo to afford 850 mg. (75% yield) of pure 4-diethylamino-1-isopropyl-[1,2,4]triazolo[4,3-a]quinoxaline as a white solid (m.p. 93°–95° C.). Mass spectrum: m/e, 283 (P). The pure product (100 mg.) was then distilled in vacuo (0.1 mm) at 140° to 150° C. to afford the analytical sample (80 mg.), m.p. 94°–96° C.

Anal. Calcd. for $C_{16}H_{21}N_5$: C, 67.82; H, 7.47; N, 24.71. Found: C, 67.56; H, 7.20; N, 24.50.

EXAMPLE 22
4-Diethylamino-1-n-propyl-[1,2,4]triazolo[4,3-a]quinoxaline

4-Chloro-1-n-propyl-[1,2,4]triazolo[4,3-a]quinoxaline (1.23 g., 0.005 mole), the product of Example 5, and 1.1 g. (0.015 mole) of diethylamine in N,N-dimethylformamide (15 ml.) were stirred at room temperature for 2 hours. The reaction mixture was then poured over ice. The precipitate was removed by filtration, washed with water and air dried. Recrystallization (twice) from ethanol/water afforded 1.1 g. (78% yield) of pure 4-diethylamino-1-n-propyl-[1,2,4]triazolo[4,3-a]quinoxaline, m.p. 92°–94° C. Mass spectrum: m/e, 283 (P).

Anal. Calcd. for $C_{16}H_{21}N_5 \cdot \frac{1}{8}H_2O$: C, 67.28; H, 7.50; N, 24.52. Found: C, 67.38; H, 7.45; N, 24.73.

EXAMPLE 23
8-Chloro-4-diethylamino-1-ethyl-[1,2,4]triazolo[4,3-a]quinoxaline (a) Preparation of 4,8-dichloro-1-ethyl-[1,2,4]triazolo[4,3-a]quinoxaline 2,6-Dichloro-3-hydrazinoquinoxaline (1.0 g., 0.0044 mole), the product of Preparation L(a), was refluxed with 15 ml. of triethyl orthopropionate for 4 hours and cooled to room temperature. The precipitate was recovered by filtration, washed with cyclohexane and air dried to afford 730 mg. (62% yield) of 4,8-dichloro-1-ethyl-[1,2,4]triazolo[4,3-a]quinoxaline, m.p. >250° C. Mass spectrum: m/e, 266 (P); m/e, 268 (P.+2).

(b) Preparation of 8-chloro-4-diethylamino-1-ethyl-[1,2,4]triazolo-[4,3-a]quinoxaline 4,8-Dichloro-1-ethyl-[1,2,4]triazolo[4,3-a]quinoxaline (7.4 g., 0.028 mole) and 6 g. (0.082 mole) of diethylamine in N,N-dimethylformamide (150 ml.) were stirred at room temperature for 4 hours. The reaction mixture was filtered and the filtrate was poured over ice. The precipitate which formed was then collected by means of filtration and taken up in chloroform. The chloroform layer was subsequently dried over anhydrous magnesium sulfate, filtered and then evacuated in vacuo to yield an off-white solid which was later recrystallized from diethyl ether/petroleum ether to afford 1.6 g. of pure 8-chloro-4-diethylamino-1-ethyl[1,2,4]-triazolo[4,3-a]quinoxaline, m.p. 105°–108° C. (decomp.).

Mass Spectrum: m/e, 303 (P); m/e, 305 (P+2).

Anal. Calcd. for $C_{15}H_{18}ClN_5$: C, 59.30; H, 5.97; N, 23.05. Found: C, 58.92; H, 5.85; N, 22.81.

EXAMPLE 24
7,8-Dichloro-4-diethylamino-1-ethyl-[1,2,4]triazolo[4,3-a]quinoxaline (a) Preparation of 2,6,7-Trichloro-3-hydrazinoquinoxaline 2,3,6,7-Tetrachloroquinoxaline (4.4 g., 0.016 mole) and 1.76 g. (0.035 mole) of hydrazine hydrate in ethanol (60 ml.) were stirred overnight at room temperature. The thick slurry was filtered and washed with ethanol to afford 4.9 g. of crude 2,6,7-trichloro-3-hydrazinoquinoxaline, m.p. <260° C.

Mass spectrum: m/e, 262 (P); m/e, 264 (P+2).

(b) Preparation of 4,7,8-Trichloro-1-ethyl-[1,2,4]triazolo[4,3-a]quinoxaline 2,6,7-Trichloro-3-hydrazinoquinoxaline (4.9 g., 0.018 mole) in triethyl orthopropionate (50 ml.) was heated at 100° C. for 2 hours. The precipitate which formed was collected by means of filtration at room temperature and washed with cyclohexane. Recrystallization from chloroform/cyclohexane two times then afforded 2.9 g. (54% yield) of pure 1,7,8-trichloro-1-ethyl-[1,2,4]triazolo[4,3-a]quinoxaline as a pink solid (m.p. 198°–201° C.).

Mass spectrum: m/e, 300 (P); m/e, 302 (P+2); m/e, 304 (P+4); m/e, 306 (P+6).

(c) Preparation of 7,8-dichloro-4-diethylamino-1-ethyl-[1,2,4]triazolo[4,3a]quinoxaline 4,7,8-Trichloro-1-ethyl-[1,2,4]-triazolo[4,3-a]quinoxaline (2.9 g., 0.0096 mole) and 2.1 g. (0.0388 mole) of diethylamine in N,N-dimethylformamide (50 ml.) were stirred at room temperature for 2 hours. The reaction mixture was poured over ice and stirred for 15 minutes. The precipitate was separated by filtration, washed with water and air dried. Recrystallization (three times) from isopropanol then afforded 500 mg. (16% yield) of pure 7,8-dichloro-4-diethylamino-1-ethyl-[1,2,4]triazolo[4,3-a]quinoxaline, m.p. 147°–149° C.

Mass spectrum: m/e, 337 (P); m/e, 339 (P+2).

Anal. Calcd. for $C_{15}H_{17}Cl_2N_5$: C, 53.26; H, 5.07; N, 20.70. Found: C, 53.05; H, 5.13; N, 20.75.

EXAMPLE 25
4-Diethylamino-1-ethyl-8-methoxy-[1,2,4]triazolo[4,3-a]quinoxaline (a) Preparation of 2-chloro-3-hydrazino-6-methoxyquinoxaline 2,3-Dichloro-6-methoxyquinoxaline (4.2 g., 0.018 mole), the product of Preparation E(b), and 2.7 ml. of hydrazine hydrate in 100 ml. of ethanol were heated under reflux for 4 hours and stirred at room temperature overnight. The precipitate was removed by filtration and washed with ethanol to afford 3.9 g. (97% yield) of 2-chloro-3-hydrazino-6-methoxyquinoxaline, m.p. <250° C.

Mass spectrum: m/e, 224 (P); m/e 226 (P+2).

(b) Preparation of 4-chloro-1-ethyl-8-methoxy-[1,2,4]triazolo[4,3-a]quinoxaline

2-Chloro-3-hydrazino-6-methoxyquinoxaline (1.3 g., 0.0058 mole) and 25 ml. of triethyl orthopropionate were heated at 100° C. for 4 hours and stirred at room temperature for 60 hours. The precipitate was removed by filtration and washed with ethanol. Recrystallization from ethanol then afforded 530 mg. (35% yield) of pure 4-chloro-1-ethyl-8-methoxy-[1,2,4]triazolo[4,3-a]quinoxaline, m.p. 196°–198° C. (decomp.).

Mass spectrum: m/e, 262 (P); m/e 264 (P+2).

(c) Preparation of 4-diethylamino-1-ethyl-8-methoxy-[1,2,4]triazolo[4,3-a]quinoxaline 4-Chloro-1-ethyl-8-methoxy-[1,2,4]triazolo[4,3-a]quinoxaline (520 mg., 0.002 mole) and 673 mg. (0.008 mole) of diethylamine in 10 ml. of N,N-dimethylformamide were stirred at room temperature overnight. The reaction mixture was poured over ice and the precipitate was separated by filtration, washed with water and air dried. Recrystallization from diethyl ether and petroleum ether then afforded 140 mg. (23% yield) of pure 4-diethylamino-1-ethyl-8-methoxy-[1,2,4]triazolo[4,3-a]quinoxaline, m.p. 135°–138° C.

Mass spectrum: m/e, 299 (P).

Anal. Calcd. for $C_{16}H_{21}N_5O \cdot \frac{1}{8}H_2O$: C, 63.71; H, 7.10; N, 23.22. Found: C, 63.63; H, 6.88; N, 23.37.

EXAMPLE 26

4-Diethylamino-1-phenyl-[1,2,4]triazolo[4,3-a]quinoxaline (a) Preparation of 4-chloro-1-phenyl-[1,2,4]triazolo[4,3-a]quinoxaline 2-Chloro-3-hydrazinoquinoxaline (2.2 g., 0.011 mole) was mixed with 6 ml. of triethyl orthobenzoate and heated at 100° C. for 30 minutes. After cooling the orange mixture to room temperature, ethanol was added. Filtration of the resultant precipitate afforded 2.1 g. of crude product which was further purified by means of trituration with warm methanol, followed by filtration and air drying to ultimately yield 1.58 g. (51%) of pure 4-chloro-1-phenyl-[1,2,4]triazolo[4,3-a]quinoxaline as an orange solid.

(b) Preparation of 4-diethylamino-1-phenyl-[1,2,4]triazolo[4,3-a]quinoxaline

To 1.58 g. (0.00563 mole) of 4-chloro-1-phenyl-[1,2,4]triazolo[4,3-a]quinoxaline dissolved in 15 ml. of N,N-dimethylformamide, there was added 1.738 ml. of diethylamine. The mixture was stirred overnight at room temperature. The precipitate which formed was collected by filtration, washed with N,N-dimethylformamide and recrystallized two times from hexane/ethyl acetate (3:1 by volume) to afford 555 mg. of pure 4-diethylamino-1-phenyl-[1,2,4]triazolo[4,3-a]quinoxaline in the form of white needles (m.p. 166°–168° C.)

Anal. Calcd. for $C_{19}H_{19}N_5$: C, 71.60; H, 5.99; N, 22.06. Found: C, 71.86; H, 5.86; N, 22.09.

EXAMPLE 27

4-Diethylamino-1-trifluoromethyl-[1,2,4]triazolo[4,3-a]quinoxaline (a) Preparation of 4-hydroxy-1-trifluoromethyl-[1,2,4]triazolo[4,3-a]quinoxaline 2-Chloro-3-hydrazinoquinoxaline (3.89 g., 0.02 mole), the product of Example 1, is added to 22.8 g. (0.20 mole) of cold trifluoroacetic acid (15.4 ml.) contained in a flame-dried reaction flask surrounded by an ice bath, while under a dry nitrogen atmosphere with the aid of mechanical stirring. The reaction mixture was then heated to 100° C. for a period of 3 hours and poured over ice. The resulting product was then collected by means of suction filtration, washed with water and air dried to constant weight. In this manner, there were ultimately obtained 3.0 g. (60%) of pure 4-hydroxy-1-trifluoromethyl-[1,2,4]triazolo[4,3-a]quinoxaline, m.p. >300° C. Mass spectrum: m/e, 254(P).

(b) Preparation of 4-chloro-1-trifluoromethyl-[1,2,4]triazolo[4,3-a]quinoxaline

In a flame-dried reaction flask under a dry nitrogen atmosphere, there were placed 3.0 g. (0.0118 mole) of 4-hydroxy-1-trifluoromethyl-[1,2,4]triazolo[4,3-a]quinoxaline and 30 ml. of phosphorus oxychloride in 2.38 g. (0.0236 mole) of triethylamine (3.3 ml.). The reaction mixture was then heated at 100° C. for a period of approximately 16 hours (i.e., overnight). Upon completion of this step, the spent mixture was cooled to room temperature, concentrated in vacuo and then partitioned between ice, water and ethanol, followed by extraction with ethyl acetate. The latter extract was next washed with saturated brine and dried over anhydrous magnesium sulfate. After removal of the drying agent by means of filtration and the solvent by means of evaporation under reduced pressure, there was obtained a residue which was subsequently dissolved in hot chloroform and filtered. The latter filtrate was then allowed to stand overnight at room temperature and filtered again. The final filtrate was then concentrated in vacuo to ultimately afford 1.4 g. of 4-chloro-1-trifluoromethyl-1,2,4]triazolo[4,3-a]quinoxaline in the form of a brownish-colored solid.

(c) Preparation of 4-diethylamino-1-trifluoromethyl-[1,2,4]triazolo[4,3-a]quinoxaline A mixture consisting of 700 mg. (0.0025 mole) of 4-chloro-1-trifluoromethyl-[1,2,4]triazolo[4,3-a]quinoxaline (prepared as described above) and 560 mg. (0.0075 mole) of diethylamine (0.8 ml.) in 10 ml. of N,N-dimethylformamide was stirred at room temperature overnight and then poured over ice. The resulting mixture was then filtered and the recovered solid product washed with water and then dissolved in ethyl acetate. The latter organic solution was next washed with saturated brine and dried over anhydrous magnesium sulfate. After removal of the drying agent by means of filtration and the solvent by means of evaporation under reduced pressure, there was ultimately obtained a light yellow solid which after recrystallization from diethyl ether gave pure 4-diethylamino-1-trifluoromethyl-

[1,2,4]triazolo[4,3-a]quinoxaline. The yield of the first crop melting at 155°–157° C. amounted to 260 mg. (34%), while the yield of the second crop melting at 153°–156° C. amounted to 170 mg. (22%).

Anal. Calcd. for $C_{14}H_{14}F_3N_5$: C, 54.37; H, 4.56; N, 22.64. Found: C, 54.08; H, 4.47; N, 23.32.

EXAMPLE 28

4-Isopropylamino-1-trifluoromethyl-[1,2,4]triazolo[4,3-a]quinoxaline

A mixture consisting of 700 mg. (0.0025 mole) of 4-chloro-1-trifluoromethyl-[1,2,4]triazolo[4,3-a]quinoxaline (the product of Example 27b) and 443 mg. (0.0075 mole) of isopropylamine (0.64 ml.) in 10 ml. of N,N-dimethylformamide was stirred at room temperature overnight and then poured over ice. The resulting mixture was then filtered and the recovered solid product washed with water and then dissolved in diethyl ether. The latter ethereal solution was next washed with saturated brine and dried over anhydrous magnesium sulfate. After removal of the drying agent by means of filtration and the solvent by means of evaporation under reduced pressure, there was ultimately obtained a white solid powder which after one recrystallization from diethyl ether yielded 550 mg. (74%) of pure 4-isopropylamino-1-trifluoromethyl-[1,2,4]triazolo[4,3-a]quinoxaline, m.p. 185°–187° C.

Anal. Calcd. for $C_{13}H_{12}F_3N_5$: C, 52.88; H, 4.10; N, 23.72. Found: C, 52.73; H, 4.00; N, 23.67.

EXAMPLE 29

1-Ethyl-4-(N-ethylacetylamino)-[1,2,4]triazolo[4,3-a]quinoxaline

A mixture consisting of 241 mg. (0.001 mole) of 1-ethyl-4-ethylamino-[1,2,4]triazolo[4,3-a]quinoxaline (the product of Example 17) and 2.5 g. (0.025 mole) of acetic anhydride (2.5 ml.) contained in a flame-dried reaction flask was refluxed (140° C.) under a dry nitrogen atmosphere for a period of three hours and then allowed to cool to room temperature. At this point, a precipitate formed and the resulting reaction mixture was poured into water and then extracted with chloroform. The chloroform extracts were combined, washed with water and subsequently dried over anhydrous magnesium sulfate. After removal of the drying agent by means of filtration and the solvent by means of evaporation under reduced pressure, there was obtained a solid product which after one recrystallization from chloroform/diethyl ether afforded 160 mg. (57%) of 1-ethyl-4-(N-ethylacetylamino)-1,2,4-triazolo[4,3-a]quinoxaline, m.p. 185°–187° C.

Anal. Calcd. for $C_{15}H_{17}N_5O$: C, 63.59; H, 6.05; N, 24.72. Found: C, 63.17; H, 6.05; N, 24.39.

EXAMPLE 30

4-Acetylamino-1-ethyl-[1,2,4]triazolo[4,3-a]quinoxaline

A mixture consisting of 533 mg. (0.0025 mole) of 4-amino-1-ethyl-[1,2,4]triazolo[4,3-a]quinoxaline (the product of Example 14) and 1.0 g. (0.01 mole) of acetic anhydride (1.0 ml.) in 20 ml. of methylene chloride was refluxed overnight (16 hours) and then allowed to cool to room temperature. The resulting clear solution was then concentrated in vacuo to afford a white solid substance that was subsequently recrystallized from chloroform/diethyl ether to yield 520 mg. (82%) of pure 4-acetylamino-1-ethyl-[1,2,4]triazolo[4,3-a]quinoxaline, m.p. 193°–195° C.

Anal. Calcd. For $C_{13}H_{13}N_5O$: C, 61.16; H, 5.13; N, 27.43. Found: C, 60.90; H, 5.26; N, 27.66.

EXAMPLE 31

4-Diacetylamino-1-ethyl-[1,2,4]triazolo[4,3-a]quinoxaline

A mixture consisting of 5.5 g. (0.0258 mole) of 4-amino-1-ethyl-[1,2,4]triazolo[4,3-a]quinoxaline (the product of Example 14) and 25 g. (0.25 mole) of acetic anhydride (25 ml.) in 60 ml. of pyridine containing 100 mg. of p-dimethylaminopyridine was stirred at room temperature overnight (~18 hours). The resulting slurry was then filtered to remove the insolubles and the orange-red filtrate was thereafter evaporated under a high vacuum to give a dark gummy residue. Upon the addition of water, pinkish-white crystals were obtained and these were subsequently collected by means of suction filtration, washed with a copious amount of water and dried in vacuo at 50° C. to ultimately afford 2.9 g. (38%) of 4-diacetylamino-1-ethyl-[1,2,4]triazolo[4,3-a]quinoxaline, m.p. 157°–159° C. Recrystallization of the latter material from ethyl acetate/diethyl ether then gave an analytically pure sample (m.p. 158°–160° C). The pure product was further characterized by means of mass spectroscopy and nuclear magnetic resonance data, in addition to elemental analysis. Mass spectrum: m/e, 297(P).

Anal. Calcd. for $C_{15}H_{15}N_5O_2$: C, 60.59; H, 5.09, N, 23.56. Found: C, 60.33; H, 5.09; N, 23.41.

EXAMPLE 32

The following [1,2,4]triazolo[4,3-a]quinoxaline-4-amine derivatives were prepared by employing the procedures described in the previous preparations and examples, starting from readily available materials in each instance:

7,8-dibromo-4-diethylamino-[1,2,4]triazolo[4,3-a]quinoxaline, m.p. 199°–201° C.

8-chloro-4-isopropylamino-[1,2,4]triazolo[4,3-a]quinoxaline, m.p. 177°–181° C.

4-ethylamino-1-trifluoromethyl-[1,2,4]triazolo[4,3-a]quinoxaline, m.p. 223°–225° C.

1-ethyl-4-ethylamino-8-methoxy-[1,2,4]triazolo[4,3-a]quinoxaline, m.p. 234°–237° C.

4-diethylamino-8-methoxy-[1,2,4]triazolo[4,3-a]quinoxaline, m.p. 124°–126° C.

8-chloro-1-ethyl-4-isopropylamino-[1,2,4]triazolo[4,3-a]quinoxaline, m.p. 189°–191° C.

4-(N-piperazino)-[1,2,4]triazolo[4,3-a]quinoxaline, m.p. 160°–162° C.

8-chloro-4-(N-piperazino)-[1,2,4]triazolo[4,3-a]quinoxaline, m.p. 253°–256° C.

8-chloro-4-(N-isopropylacetylamino)-[1,2,4]triazolo[4,3-a]quinoxaline, m.p. 148°–151° C.

4-acetylamino-8-chloro-1-ethyl-[1,2,4]triazolo[4,3-a]quinoxaline, m.p. 203°–205° C.

8-chloro-1-ethyl-4-(N-isopropylacetylamino)-1,2,4triazolo[4,3-a]quinoxaline, m.p. 155°–158° C.

7,8-dichloro-4-(N-isopropylacetylamino)-[1,2,4]triazolo[4,3-a]quinoxaline, m.p. 207°–210° C.

4-amino-7,8-dichloro-1-ethyl-[1,2,4]triazolo[4,3-a]quinoxaline, m.p. >260° C.

4-amino-8-chloro-1-ethyl-[1,2,4]triazolo[4,3-a]quinoxaline, m.p. 248°–253° C.

4-acetylamino-7,8-dichloro-1-ethyl-[1,2,4]triazolo[4,3-a]quinoxaline, m.p. 230°-232° C.

8-fluoro-4-isopropylamino-[1,2,4]triazolo[4,3-a]quinoxaline, m.p. 215°-217° C.

4-ethylamino-8-fluoro-[1,2,4]triazolo[4,3-a]quinoxaline, m.p. 239°-242° C.

1-ethyl-8-fluoro-4-isopropylamino-[1,2,4]triazolo[4,3-a]quinoxaline, m.p. 209°-212° C.

7,8-difluoro-4-isopropylamino-[1,2,4]triazolo[4,3-a]quinoxaline, m.p. 218°-221° C.

1-ethyl-4-ethylamino-8-fluoro-[1,2,4]triazolo[4,3-a]quinoxaline, m.p. 231°-233° C.

7,8-difluoro-4-ethylamino-[1,2,4]triazolo[4,3-a]quinoxaline, m.p. 208°-211° C.

4-diethylamino-8-fluoro-[1,2,4]triazolo[4,3-a]quinoxaline, m.p. 151°-153° C.

4-diethylamino-1-ethyl-8-fluoro-[1,2,4]triazolo[4,3-a]quinoxaline, m.p. 94°-97° C.

7-chloro-4-dimethylamino-1-ethyl-[1,2,4]triazolo[4,3-a]quinoxaline methanesulfonate (mesylate), m.p. 214°-217° C.

7-chloro-4-diethylamino-1-ethyl-[1,2,4]triazolo[4,3-a]quinoxaline methanesulfonate, m.p. 172°-175° C.

7,8-dichloro-1-ethyl-4-(N-piperazino)-[1,2,4]triazolo[4,3-a]quinoxaline methanesulfonate, m.p. 252°-255° C.

7,8-dichloro-4-dimethylamino-1-ethyl-[1,2,4]triazolo[4,3-a]quinoxaline, m.p. 168°-171° C.

7,8-dichloro-4-dimethylamino-1-ethyl-[1,2,4]triazolo[4,3-a]quinoxaline methanesulfonate, m.p. 216°-219° C.

4-acetylamino-1-ethyl-8-fluoro-[1,2,4]triazolo[4,3-a]quinoxaline, m.p. 203°-205° C.

4-amino-7-chloro-1-ethyl-[1,2,4]triazolo[4,3-a]quinoxaline methanesulfonate, m.p. 240°-243° C.

7-chloro-1-ethyl-4-ethylamino-[1,2,4]triazolo[4,3-a]quinoxaline methanesulfonate, m.p. 187°-189° C.

7-chloro-4-diethylamino-[1,2,4]triazolo[4,3-a]quinoxaline methanesulfonate, m.p. 205°-207° C.

4-diethylamino-7,8-difluoro-[1,2,4]triazolo[4,3-a]quinoxaline methanesulfonate, m.p. 220°-223° C.

4-acetylamino-7-chloro-1-ethyl-[1,2,4]triazolo[4,3-a]quinoxaline, m.p. 210°-212° C.

8-chloro-1-ethyl-4-ethylamino-[1,2,4]triazolo[4,3-a]quinoxaline methanesulfonate, m.p. 235°-238° C.

4-amino-7-chloro-[1,2,4]triazolo[4,3-a]quinoxaline methanesulfonate, m.p. 279°-282° C.

4-amino-8-chloro-1-methyl-[1,2,4]triazolo[4,3-a]quinoxaline methanesulfonate, m.p. 213°-215° C.

8-chloro-4-isopropylamino-1-trifluoromethyl-[1,2,4]triazolo[4,3-a]quinoxaline methanesulfonate, m.p. 183°-185° C.

8-chloro-4-diethylamino-1-methyl-[1,2,4]triazolo[4,3-a]quinoxaline methanesulfonate, m.p. 172°-175° C.

4-diacetylamino-[1,2,4]triazolo[4,3-a]quinoxaline, 211°-214° C.

4-diacetylamino-8-chloro-[1,2,4]triazolo[4,3-a]quinoxaline, m.p. 208°-210° C.

8-chloro-4-isopropylamino-1-methyl-[1,2,4]triazolo[4,3-a]quinoxaline methanesulfonate, m.p. 206°-208° C.

4-acetylamino-1-methyl-8-chloro-[1,2,4]triazolo[4,3-a]quinoxaline, m.p. 262°-264° C.

8-chloro-1-ethyl-4-trimethylacetylamino-[1,2,4]triazolo[4,3-a]quinoxaline, m.p. 211°-213° C.

7,8-difluoro-1-ethyl-4-isopropylamino-[1,2,4]triazolo[4,3-a]quinoxaline methanesulfonate, m.p. 151°-152° C.

4-n-butyrylamino-8-chloro-1-ethyl-[1,2,4]triazolo[4,3-a]quinoxaline, m.p. 185°-187° C.

8-chloro-4-diethylamino-1-trifluoromethyl-[1,2,4]triazolo[4,3-a]quinoxaline hydrate, m.p. 135°-136° C.

4-amino-8-chloro-1-trifluoromethyl-[1,2,4]triazolo[4,3-a]quinoxaline methanesulfonate, m.p. 259°-261° C.

4-ethylamino-8-fluoro-1-trifluoromethyl-[1,2,4]triazolo[4,3-a]quinoxaline methanesulfonate, m.p. 180°-183° C.

8-fluoro-4-isopropylamino-1-trifluoromethyl-[1,2,4]triazolo[4,3-a]quinoxaline methanesulfonate, m.p. 185°-188° C.

4-diethylamino-7,8-difluoro-1-ethyl-[1,2,4]triazolo[4,3-a]quinoxaline, m.p. 109°-111° C.

1-ethyl-4-ethylamino-7-fluoro-[1,2,4]triazolo[4,3-a]quinoxaline methanesulfonate, m.p. 215°-219° C.

4-amino-7-methoxy-[1,2,4]triazolo[4,3-a]quinoxaline methanesulfonate, m.p. 262°-264° C.

8-chloro-4-isopropylamino-1-phenyl-[1,2,4]triazolo[4,3-a]quinoxaline, m.p. 183°-186° C.

8-chloro-4-ethylamino-1-phenyl-[1,2,4]triazolo[4,3-a]quinoxaline, m.p. 254°-256° C.

7-fluoro-4-isopropylamino-[1,2,4]triazolo[4,3-a]quinoxaline methanesulfonate, m.p. 214°-216° C.

4-ethylamino-7-fluoro-[1,2,4]triazolo[4,3-a]quinoxaline methanesulfonate, m.p. 216°-218° C.

4-diethylamino-8-fluoro-1-trifluoromethyl-[1,2,4]triazolo[4,3-a]quinoxaline, m.p. 146°-149° C.

7,8-dichloro-1-ethyl-4-isopropylamino-[1,2,4]triazolo[4,3-a]quinoxaline, m.p. 197°-198° C.

8-chloro-4-diethylamino-1-phenyl-[1,2,4]triazolo[4,3-a]quinoxaline, m.p. 194°-195° C.

4-acetylamino-1-ethyl-7-fluoro-[1,2,4]triazolo[4,3-a]quinoxaline, m.p. 273°-275° C.

4-acetylamino-8-chloro-1-trifluoromethyl-[1,2,4]triazolo[4,3-a]quinoxaline, m.p. 215°-216° C.

4-amino-8-chloro-1-phenyl-[1,2,4]triazolo[4,3-a]quinoxaline methanesulfonate, m.p. 273°-275° C.

8-chloro-4-ethylamino-1-trifluoromethyl-[1,2,4]triazolo[4,3-a]quinoxaline, m.p. 228°-230° C.

1-ethyl-7-fluoro-4-isopropylamino-[1,2,4]triazolo[4,3-a]quinoxaline methanesulfonate, m.p. 178°-181° C.

4-amino-8-fluoro-1-trifluoromethyl-[1,2,4]triazolo[4,3-a]quinoxaline hydrate, m.p. 260°-263° C.

8-chloro-1-ethyl-4R-phenylisopropylamino-[1,2,4]triazolo[4,3-a]quinoxaline, m.p. 155°-157° C.

4-amino-1-ethyl-7-fluoro-[1,2,4]triazolo[4,3-a]quinoxaline, m.p. 285°-289° C.

4-amino-1-ethyl-7-methoxy-[1,2,4]triazolo[4,3-a]quinoxaline methanesulfonate, m.p. 255°-258° C.

4-acetylamino-8-fluoro-1-trifluoromethyl-[1,2,4]triazolo[4,3-a]quinoxaline, m.p. 217°-219° C.

4-acetylamino-1-ethyl-7-methoxy-[1,2,4]triazolo[4,3-a]quinoxaline, m.p. 202°-205° C.

8-chloro-1-ethyl-4S-phenylisopropylamino-[1,2,4]triazolo[4,3-a]quinoxaline, m.p. 156°-157° C.

4-acetylamino-8-fluoro-[1,2,4]triazolo[4,3-a]quinoxaline, m.p. 240°-242° C.

4-acetylamino-[1,2,4]triazolo[4,3-a]quinoxaline, m.p. 269°-272° C.

4-amino-7-fluoro-[1,2,4]triazolo[4,3-a]quinoxaline methanesulfonate, m.p. 246°-248° C.

4-amino-8-fluoro-[1,2,4]triazolo[4,3-a]quinoxaline methanesulfonate, m.p. 176°-178° C.

4-acetylamino-7-fluoro-[1,2,4]triazolo[4,3-a]quinoxaline, m.p. 290°-292° C.

8-chloro-4-isopropylamino-1-pentafluoroethyl-[1,2,4]triazolo[4,3-a]quinoxaline, m.p. 171°–174° C.

EXAMPLE 33

8-Chloro-1-ethyl-4-propionylamino-[1,2,4]triaxolo[4,3-a]quinoxaline

A mixture consisting of 1.25 g. (0.005 mole) of 4-amino-8-chloro-1-ethyl-[1,2,4]triazolo[4,3-a]quinoxaline (m.p. 248°–253° C.), a product reported in Example 32, and 15 ml. of propionic anhydride was refluxed overnight for a period of approximately 16 hours and then cooled to room temperature (~20° C.). Upon completion of this step, the resulting reaction mixture was filtered and the recovered precipitate was subsequently dissolved in chloroform. The latter organic solution was then filtered and thereafter successively washed with water, saturated aqueous sodium bicarbonate solution and saturated brine, followed by drying over anhydrous magnesium sulfate. After removal of the drying agent by means of filtration and the solvent by means of evaporation under reduced pressure, there was obtained a residual material that was subsequently chromatographed on a 150 ml. silica gel column and then eluted with chloroform/methanol (95:5 by volume). Like fractions containing the product were combined and thereafter concentrated in vacuo to yield a crystalline material, which was later recrystallized from chloroform/ethyl ether to ultimately afford 540 mg. (36%) of pure 8-chloro-1-ethyl-4-propionylamino-[1,2,4]triazolo[4,3-a]quinoxaline, m.p. 212°–215° C.

Anal. Calcd. for $C_{14}H_{14}ClN_5O$: 55.36; H, 4.64; N, 23.06. Found: C, 54.91; H, 4.59; N, 22.76.

I claim:

1. A pharmaceutical composition in unit dosage form for use in the treatment of depression and fatigue comprising a pharmaceutically acceptable carrier and an antidepressant/anti-fatigue effective amount of a compound selected from the group consisting of [1,2,4]triazolo[4,3-a]quinoxaline-4-amine bases of the formula:

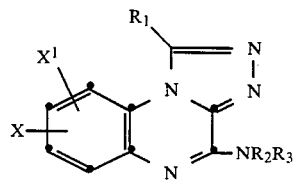

and the pharmaceutically acceptable acid addition salts thereof, wherein

X and $X^1$ are each selected from the group consisting of hydrogen, fluorine, chlorine, bromine and methoxy;

$R_1$ is selected from the group consisting of hydrogen, lower alkyl, lower perfluoroalkyl and phenyl; and $R_2$ and $R_3$ are each selected from the group consisting of hydrogen, lower alkyl, phenylalkyl having up to three carbon atoms in the alkyl moiety and alkanoyl having from two to five carbon atoms, provided that at least one of X, $X^1$ and $R_1$ is always other than hydrogen or lower alkyl when each of $R_2$ and $R_3$ is hydrogen or lower alkyl; or $R_2$ and $R_3$, when taken together, complete a piperazino ring.

2. A pharmaceutical composition as claimed in claim 1 wherein X and $X^1$ are each hydrogen, Rl is trifluoromethyl, and $R_2$ and $R_3$ are each hydrogen or lower alkyl.

3. A pharmaceutical composition as claimed in claim 1 wherein X and $X^1$ are each hydrogen, $R_1$ is lower alkyl and $R_3$ is acetyl.

4. A pharmaceutical composition as claimed in claim 3 wherein $R_1$ is ethyl and $R_2$ is hydrogen.

5. A pharmaceutical composition as claimed in claim 3 wherein $R_1$ and $R_2$ are both ethyl.

6. A pharmaceutical composition as claimed in claim 3 wherein $R_1$ is ethyl and $R_2$ is acetyl.

7. A pharmaceutical composition as claimed in claim 1 wherein at least one of X and $X^1$ is fluorine, $R_1$ and $R_2$ are each hydrogen and R is lower alkyl.

8. A pharmaceutical composition as claimed in claim 7 wherein X is fluorine at the 8-position of the molecule and $R_3$ is isopropyl.

9. A pharmaceutical composition as claimed in claim 7 wherein X is fluorine at the 7-position of the molecule, $X^1$ is fluorine at the 8-position of the molecule and $R_3$ is isopropyl.

10. A pharmaceutical composition as claimed in claim 1 wherein at least one of X and $X^1$ is chlorine, $R_1$ is lower alkyl or trifluoromethyl, $R_2$ is hydrogen and $R_3$ is hydrogen lower alkyl or alkanoyl having two to five carbon atoms.

11. A pharmaceutical composition as claimed in claim 10 wherein X is hydrogen, $X^1$ is chlorine at the 8-position of the molecule, $R_1$ is ethyl and $R_3$ is isopropyl.

12. A pharmaceutical composition as claimed in claim 10 wherein X is hydrogen, $X^1$ is chlorine at the 8-position of the molecule, $R_1$ is ethyl and $R_3$ is propionyl.

13. A pharmaceutical composition as claimed in claim 10 wherein X is hydrogen, $X^1$ is chlorine at the 8-position of the molecule, $R_1$ is trifluoromethyl and $R_3$ is hydrogen 14. A pharmaceutical composition as claimed in claim 10 wherein X is hydrogen, $X^1$ is chlorine at the 8-position of the molecule, $R_1$ is trifluoromethyl and $R_3$ is acetyl.

15. A pharmaceutical composition as claimed in claim 10 wherein X is hydrogen, $X^1$ is chlorine at the 8-position of the molecule, $R_1$ is trifluoromethyl and $R_3$ is isopropyl.

16. A pharmaceutical composition as claimed in claim 10 wherein X is hydrogen, $X^1$ is chlorine at the 8-position of the molecule, $R_1$ is ethyl and $R_3$ is acetyl.

17. A pharmaceutical composition as claimed in claim 10 wherein X is chlorine at the 7-position of the molecule, $X^1$ is chlorine at the 8-position of the molecule, $R_1$ is ethyl and $R_3$ is hydrogen.

18. A pharmaceutical composition as claimed in claim 1 wherein at least one of X and $X^1$ is fluorine, $R_1$ is trifluoromethyl, $R_2$ is hydrogen and $R_3$ is hydrogen, lower alkyl or alkanoyl having from two the five carbon atoms.

19. A pharmaceutical composition as claimed in claim 18 wherein X is hydrogen, $X^1$ is fluorine at the 8-position of the molecule and $R_3$ is hydrogen.

20. A pharmaceutical composition as claimed in claim 18 wherein X is hydrogen, $X^1$ is fluorine at the 8-position of the molecule and $R_3$ is isopropyl.

21. A pharmaceutical composition as claimed in claim 18 wherein X is hydrogen, $X^1$ is fluorine at the 8-position of the molecule and $R_3$ is acetyl.

22. A pharmaceutical composition in unit dosage form for use in the treatment of depression and fatigue comprising an antidepressant/anti-fatigue effective amount of a compound selected from the group consisting of [1,2,4]triazolo[4,3-a]quinoxaline-4-amine bases of the formula:

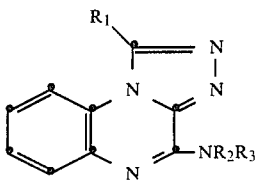

and the pharmaceutically acceptable acid addition salts thereof, wherein $R_1$ and $R_2$ are each hydrogen and $R_3$ is ethyl or isopropyl;

$R_1$ is hydrogen or methyl, and $R_2$ and $R_3$ are each ethyl;

$R_1$ is ethyl, $R_2$ is hydrogen and $R_3$ is hydrogen, methyl or ethyl; and $R_1$ is ethyl, and $R_2$ and $R_3$ are each methyl or ethyl.

23. A pharmaceutical composition as claimed in claim 22 wherein $R_1$ and $R_2$ are each hydrogen and $R_3$ is ethyl.

24. A pharmaceutical composition as claimed in claim 22 wherein $R_1$ is ethyl, $R_2$ is hydrogen and $R_3$ is ethyl.

25. A pharmaceutical composition as claimed in claim 22 wherein $R_1$, $R_2$ and $R_3$ are each ethyl.

* * * * *